(12) United States Patent
Bjarklev et al.

(10) Patent No.: US 6,853,457 B2
(45) Date of Patent: Feb. 8, 2005

(54) OPTICAL AMPLIFICATION IN COHERENCE REFLECTOMETRY

(75) Inventors: Anders Bjarklev, Roskilde (DK);
Andreas Tycho, Copenhagen Ø (DK);
Peter E. Andersen, Frederiksberg (DK)

(73) Assignee: Forskningscenter Riso (DK)

( * ) Notice: Subject to any disclaimer, the term of this patent is extended or adjusted under 35 U.S.C. 154(b) by 0 days.

(21) Appl. No.: 10/363,323

(22) PCT Filed: Sep. 4, 2001

(86) PCT No.: PCT/DK01/00573
§ 371 (c)(1),
(2), (4) Date: May 2, 2003

(87) PCT Pub. No.: WO02/21074
PCT Pub. Date: Mar. 14, 2002

(65) Prior Publication Data
US 2003/0184758 A1 Oct. 2, 2003

(30) Foreign Application Priority Data
Sep. 4, 2000 (DK) .......................... 2000 01318

(51) Int. Cl.⁷ .............................................. G01B 9/02
(52) U.S. Cl. ...................................... 356/497; 356/479
(58) Field of Search ................................ 356/479, 497, 356/450

(56) References Cited

U.S. PATENT DOCUMENTS

| | | | |
|---|---|---|---|
| 4,936,833 A | 6/1990 | Sams | 604/232 |
| 5,013,907 A | 5/1991 | Bateman | 250/227.12 |
| 5,226,895 A | 7/1993 | Harris | 604/208 |
| 5,267,016 A | 11/1993 | Meinzer et al. | 356/358 |
| 5,291,267 A | 3/1994 | Sorin et al. | 356/345 |
| 5,321,501 A | 6/1994 | Swanson et al. | 356/345 |
| 5,371,587 A | 12/1994 | de Groot et al. | 356/349 |

(List continued on next page.)

FOREIGN PATENT DOCUMENTS

WO    WO 99/46557    9/1999

OTHER PUBLICATIONS

"In Vivo Ultrahigh–Resolution Optical Coherence Tomography", Optics Letters (1999), vol. 24, No. 17, 1221–1223.
"Unbalanced Versus Balanced Operation in An Optical Coherence Tomography Systems", Applied Optics (2000), vol. 39, No. 1, 173–182.

(List continued on next page.)

Primary Examiner—Zandra V. Smith
Assistant Examiner—Andrew H. Lee
(74) Attorney, Agent, or Firm—Gifford, Krass, Groh, Sprinkle, Anderson & Citkowski, P.C.

(57) ABSTRACT

The present invention relates to an apparatus and a method for optical coherence reflectometry, in particular for optical coherence tomography. The invention particularly relates to the route of the light field in the sample arm. The reflected light field in the sample arm is amplified before being received by a combining means, said combining means being capable of receiving the reflected light field from the sample arm as well as the second reflected light field from the reference arm. Thereby, it is possible to direct substantially all light energy in the sample arm to the combining means, and to obtain fully the utilisation of the amplification of the reflected light field since preferably only the reflected light field is amplified by the optical amplifier. This leads to an improved signal-to-noise ratio (SNR) whereby an increase of the maximal penetration depth is obtained. Thereby, the apparatus is useful for obtaining optical biopsies of transparent as well as non-transparent tissues as well as new technical fields wherein the increased SNR allows the use of the present apparatus.

55 Claims, 15 Drawing Sheets

U.S. PATENT DOCUMENTS

| | | | | |
|---|---|---|---|---|
| 5,434,662 | A | | 7/1995 | Rockwell et al. .......... 356/4.01 |
| 5,459,564 | A | * | 10/1995 | Chivers .................... 356/73.1 |
| 5,459,570 | A | | 10/1995 | Swanson et al. ............ 356/345 |
| 5,465,147 | A | * | 11/1995 | Swanson .................... 356/497 |
| 5,549,575 | A | | 8/1996 | Giambattista et al. ...... 604/232 |
| 5,688,251 | A | | 11/1997 | Chanoch .................... 604/208 |
| 5,760,901 | A | | 6/1998 | Hill ............................ 356/345 |
| 5,921,926 | A | | 7/1999 | Rolland et al. ............. 600/407 |
| 5,956,355 | A | | 9/1999 | Swanson et al. ............... 372/20 |
| 5,975,697 | A | | 11/1999 | Podoleanu et al. ......... 351/206 |
| 6,002,480 | A | | 12/1999 | Izatt et al. .................. 356/345 |
| 6,004,314 | A | | 12/1999 | Wei et al. ..................... 606/12 |
| 6,020,963 | A | | 2/2000 | DiMarzio ................... 356/351 |
| 6,038,055 | A | | 3/2000 | Hansch et al. .............. 359/279 |
| 6,047,218 | A | | 4/2000 | Whayne et al. ............. 607/122 |
| 6,053,613 | A | | 4/2000 | Wei et al. .................... 351/205 |
| 6,057,920 | A | | 5/2000 | Fercher et al. .............. 356/357 |
| 6,160,826 | A | | 12/2000 | Swanson et al. ............... 372/20 |
| 6,233,055 | B1 | | 5/2001 | Mandella et al. ........... 356/479 |
| 6,252,666 | B1 | | 6/2001 | Mandella et al. ........... 356/479 |
| 6,307,633 | B1 | * | 10/2001 | Mandella et al. ........... 356/479 |
| 6,485,413 | B1 | * | 11/2002 | Boppart et al. ............. 600/160 |
| 6,501,551 | B1 | * | 12/2002 | Tearney et al. ............. 356/477 |
| 6,680,779 | B2 | * | 1/2004 | Toida ......................... 356/479 |

OTHER PUBLICATIONS

"Self–Phase–Modulated Kerr–lens Mode–Locked Cr:forsterite Laser Source for Optical Coherence Tomography", Bouma et al., Optics Letters (1996) vol. 21, No. 22, 1839–1841.

"Time–Gated Transillumination of Objects in Highly Scattering Optical Amplifier", Marengo et al., IEEE Journal of Selected Topics in Quantum Electronics (1999), vol. 5, No. 4, 895–901.

"OCT Scanner Requires No Moving Parts", Hassaun Jones–Bey, Laser, Focus World (1999) 32–34.

"Spatially Resolved Spectral Interferometry for Determination of Subsurface Structure", Zuluaga et al., Optics Letters (1999) vol. 24, No. 8, 519–521.

"Noise in Optical Low–Coherence Reflectometry", Takada, K., IEEE Journal of Quantum Electronics (1998), vol. 34, No. 7, 1098–1108.

* cited by examiner

OPTICAL AMPLIFICATION IN COHERENCE REFLECTOMETRY

This application is the national phase under 35 U.S.C. § 371 of PCT International Application No. PCT/DK01/00573 which has an International filing date of Sep. 4, 2001, which designated the United States of America.

The present invention relates to an apparatus for optical coherence reflectometry, in particular for optical coherence tomography.

BACKGROUND

Optical low-coherence reflectometry (OLCR) is used for example for analyzing inhomogeneities in optical waveguides and optical devices. In this method light is transmitted down the optical fibre and light resulting from the interaction with an inhomogeneity in the optical fibre is back-scattered. The light is split into two arms; a sample arm and a reference arm. When the optical pathlength in the sample arm matches the pathlength in the reference arm coherent interference occurs and the distance the light has travelled in the sample arm may be determined.

Optical low-coherence reflectometry is also used in the imaging of 2-dimensional and 3 dimensional structures, eg. biological tissues, in this respect often referred to as optical coherence tomography (OCT). OCT can be used to perform high-resolution cross-sectional in vivo and in situ imaging of microstructures, such as in transparent as well as non-transparent biological tissue or other absorbing and/or random media in generel. There are a number of applications for OCT, such as non-invasive medical diagnostic tests also called optical biopsies. For example cancer tissue and healthy tissue can be distinguished by means of different optical properties.

OLCR can be extended through the use of polarized light. The light field towards the reference and sample is then polarized. After combining the light reflected from the reference and the sample, the combined light field is split up again into two new light fields with perpendicular polarization states. Through this method the birefringent properties of the sample can be investigated in addition to the information obtainable with ordinary OLCR adding to the systems ability to discriminate between certain types of materials within the sample. This method also applies to OCT often referred to as polarization sensitive OCT (PS-OCT).

In order to optimize optical low-coherence reflectometry measurements and imaging various suggestions to increase signal-to-noise ratio (SNR) have been discussed in the art.

U.S. Pat. No. 5,291,267 (Sorin et al.) discloses optical reflectometry for analyzing inhomogeneities in optical fibres. In U.S. Pat. No. 5,291,267 amplification of the light reflected from the optical fibre is conducted. In particular U.S. Pat. No. 5,291,267 suggests to use the light source as an amplifier in order to save costs.

WO 99/46557 (Optical Biopsies Technologies) discusses SNR in a system wherein a reference beam is routed into a long arm of an interferometer by a polarizing beamsplitter. In general the reference suggest to include an attenuator in the reference arm to increase SNR. In a balanced setup the reference on the other hand suggests to increase the power of the reference arm in order to increase SNR.

In "Unbalanced versus balanced operation in an optical coherence tomography system" Podoleanu, A. G., Vol. 39, No. 1, Applied optics, discussed various methods of increasing SNR in unbalanced and balanced systems, respectively. Reduction of power in the reference arm was suggested as well as reduction of fibre end reflections to increase the SNR.

The present invention relates to an optimisation of optical low-coherence reflectometry whereby an increase of the SNR is obtained leading to a better result of the measurements, in particular in relation to penetration depth of the system, so that the penetration depth increases, when the SNR increases.

SUMMARY OF THE INVENTION

Thus, the present invention relates to an apparatus for optical coherence reflectometry comprising a light source for providing a light signal splitting means for dividing said light signal into a first light field and a second light field, means for directing the first light field to a sample, and means for directing a first reflected light field from the sample, wherein an optical amplifier is inserted in the first reflected light field, said optical amplifier being different from the light source, and means for directing the amplified first reflected light field to a combining means, so that the amplified first reflected light field is directed to the combining means through another route than a route through the splitting means for dividing the light signal, means for directing the second light field to a reference path comprising a reflecting means, and means for directing a second reflected light field from the reference path to the combining means, combining means for receiving said amplified first reflected light field and said second reflected light field to generate a combined light signal, and at least one detecting means for detecting the combined light signal and outputting detection signals.

In the present context the term "optical coherence reflectometry" is used in its normal meaning, and thereby equivalent to "optical low-coherence reflectometry, OLCR" and in particular the term means optical coherence tomography, OCT, and polarisation-sensitive optical coherence tomography, PS-OCT.

The present apparatus offers a better signal-to-noise ratio (SNR) whereby an increase of the maximal penetration depth is obtained. Thereby, the apparatus according to the present invention is especially useful for obtaining optical biopsies of transparent as well as non-transparent tissues.

In particular a combination of the arrangement of amplification discussed above and reduction of fibre end reflections increases the signal-to-noise ratio leading to an improved system.

The term "sample path" or "sample arm" is used to define the route travelled by the light from the light source to the sample and reflected from the sample to the combining means. In the present context the light field and routes relating to the sample arm is denoted the first light field and the first light route, respectively.

Correspondingly the term "reference path" or "reference arm" is used to define the route travelled by the light from the light source to the reference reflection means and reflected from the reflection means to the combining means. In the present context the light field and routes relating to the reference arm is denoted the second light field and the second light route, respectively.

In another aspect the present invention relates to a method for providing a result of a sample comprising establishing a light source for providing a light signal, splitting said light signal into a first light field and a second light field, directing the first light field to a sample, and the second light field to a reference path, receiving the first reflected light field from the sample, optically amplifying the first reflected light field, and directing the first reflected light field in a combining means, receiving the second reflected light field, combining said amplified first reflected light field and said second reflected light field to generate a combined light signal, detecting the combined light signal obtaining detection signals, and processing the detection signals obtaining the result of the sample.

In the present context the term "result of the sample" refers in OCT to the image of the tissue obtained. When using the present invention in OLCR in optical fibres used for example in the communication technology the result relates to the signal obtained, such as a signal relating to the distance to an inhomogeneity in the device under test.

DRAWINGS

FIG. 1 shows an unbalanced conventional OCT system according to prior art, wherein an attenuator has been inserted in the reference arm.

FIG. 2 shows a balanced apparatus according to the invention, wherein the amplified first reflected light field is directed to the combining means through another route than a route through the splitting means. A y-coupler is inserted in the sample arm to receive the reflected light field from the sample.

FIG. 3 shows the balanced detection means of FIG. 2 in detail.

FIG. 4 shows a balanced apparatus as in FIG. 2 wherein an optical circulator has been inserted instead of the beam splitting means in the sample.

FIG. 5 shows a balanced system according to prior art chosen as reference system. The system is similar to the system shown in FIG. (2) except for omittion of the optical amplifier and the y-coupler in the sample part. The y-coupler is omitted since it is no longer necessary for the light to follow a different path to and from the sample.

FIG. 6 shows the optimum splitter ratio for the system shown in FIG. (2) investigated in the absence of an optical amplifier, i.e. the amplification factor is set to 1 and the optical noise added from the amplifier is set to zero. The SNR of the system is compared to the reference system, where both systems are used in the uncoated case.

FIG. 7 shows the optimum splitter ratio for the system shown in FIG. (2) investigated in the absence of an optical amplifier, i.e. the amplification factor is set to 1 and the optical noise added from the amplifier is set to zero. The SNR of the system is compared to the reference system, where both systems are used in the coated case.

FIG. 8 shows the effect of including an optical amplifier on the novel system shown in FIG. (2). The SNR of the novel system is compared to the reference system FIG.(5), where both systems are used in the uncoated case.

FIG. 9 shows the effect of including an optical amplifier on the novel system shown in FIG. (2). The SNR of the novel system is compared to the reference system FIG.(5), where both systems are used in the coated case.

FIG. 10 shows the optimum splitting ratio for the novel system shown in FIG. (2), with the optical amplifier set at a fixed amplification factor of 20 dB. The SNR of the novel system is compared to the reference system FIG.(5), where both systems are used in the uncoated case.

FIG. 11 shows the optimum splitting ratio for the novel system shown in FIG. (2), with the optical amplifier set at a fixed amplification factor of 20 dB. The SNR of the novel system is compared to the reference system FIG.(5), where both systems are used in the coated case.

FIG. 12 shows the relative SNR shown as function of the thermal noise for the system shown in FIG. (4), where the splitting ratio is set to the optimum setting and $\Gamma_{incoh}$ is taken as the coated case.

FIG. 13 shows a balanced apparatus according to the invention, wherein only the first reflected light field is amplified by the optical amplifier and hereafter directed to the combining means.

FIG. 14 shows the SNR of the system shown in FIG. (5) as a function of the splitting ratio $x/(1-x)$ in the uncoated case. The optimum splitting ratio, for the set of parameter values chosen as an example, is found to be 33.4/66.6, and for the uncoated case, this splitting ratio is used in the reference system.

FIG. 15 shows the SNR of the system shown in FIG. (5) as a function of the splitting ratio $x/(1-x)$ in the coated case. The optimum splitting ratio for the set of parameter values chosen as an example is found to be 33.4/66.6, and for the coated case, this splitting ratio is used in the reference system.

FIG. 16 shows the effect of the optical amplifier in the novel system in FIG. (13) as a function of amplification factor. A splitting ratio of 50/50 has been chosen for the novel system whereas the optimum splitting ratio is used for the reference system. The novel system in FIG. (13) and the reference system FIG. (5) are both used in the uncoated case. Relative SNR refers to the SNR of the novel system divided by the optimum SNR of the reference system.

FIG. 17 shows the effect of the optical amplifier in the novel system in FIG. (13) as a function of amplification factor. A splitting ratio of 50/50 has been chosen for the novel system whereas the optimum splitting ratio is used for the reference system. The novel system in FIG. (13) and the reference system FIG. (5) are both used in the coated case. Relative SNR refers to the SNR of the novel system divided by the optimum SNR of the reference system.

FIG. 18 shows the SNR of the novel system shown in FIG. (13), relative to the optimum reference system, as a function of the splitting ratio $x/(1-x)$ in the uncoated case. The optical amplifier is set at a fixed amplification factor of 20 dB. The optimum splitting ratio for the set of parameter values chosen as an example is found to be 45.1/54.9.

FIG. 19 shows the SNR of the novel system shown in FIG. (13), relative to the optimum reference system, as a function of the splitting ratio $x/(1-x)$ in the uncoated case. The optical amplifier is set at a fixed amplification factor of 20 dB. The optimum splitting ratio for the set of parameter values chosen as an example is found to be 45.1/54.9.

FIG. 20 shows the SNR of the novel system shown in FIG. (4), relative to the optimum reference system, as a function of the splitting ratio $x/(1-x)$ in the uncoated case. The optical amplifier is set at a fixed amplification factor of 20 dB. The optimum splitting ratio for the set of parameter values chosen as an example is found to be 73.3/26.7.

FIG. 21 shows the SNR of the novel system shown in FIG. (4), relative to the optimum reference system, as a function of the splitting ratio $x/(1-x)$ in the coated case. The optical amplifier is set at a fixed amplification factor of 20 dB. The optimum splitting ratio for the set of parameter values chosen as an example is found to be 73.5/26.5.

FIG. 22 shows the relative SNR of the novel system shown in FIG. (4), relative to the optimum reference system, as a function of the noise contribution of the receiver. The system is used in the coated case and the splitting ratio is set to the optimum found in FIG. (21).

Figure 3:
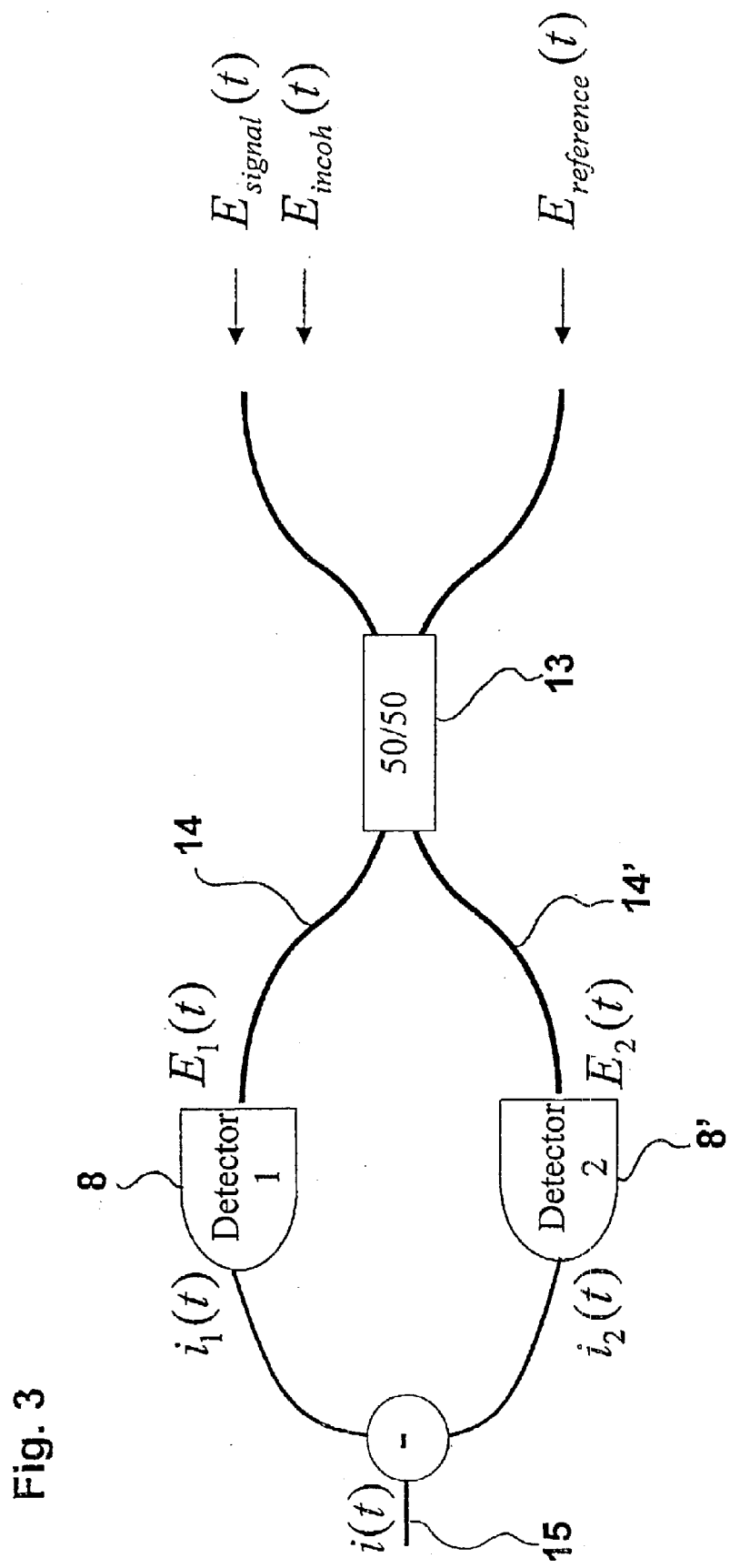

The balanced detection means 11 is shown in detail in FIG. 3 comprising a combining means 13, exemplified by a splitter having a splitting ratio of 50/50, capable of splitting the combined signal into first split signal 14 and second split signal 14'. The split signals 14, 14' are directed to the detectors 8, 8' respectively. The detected signal may be output via 15 to a printing means, a display and/or a storage means.

Figure 4:
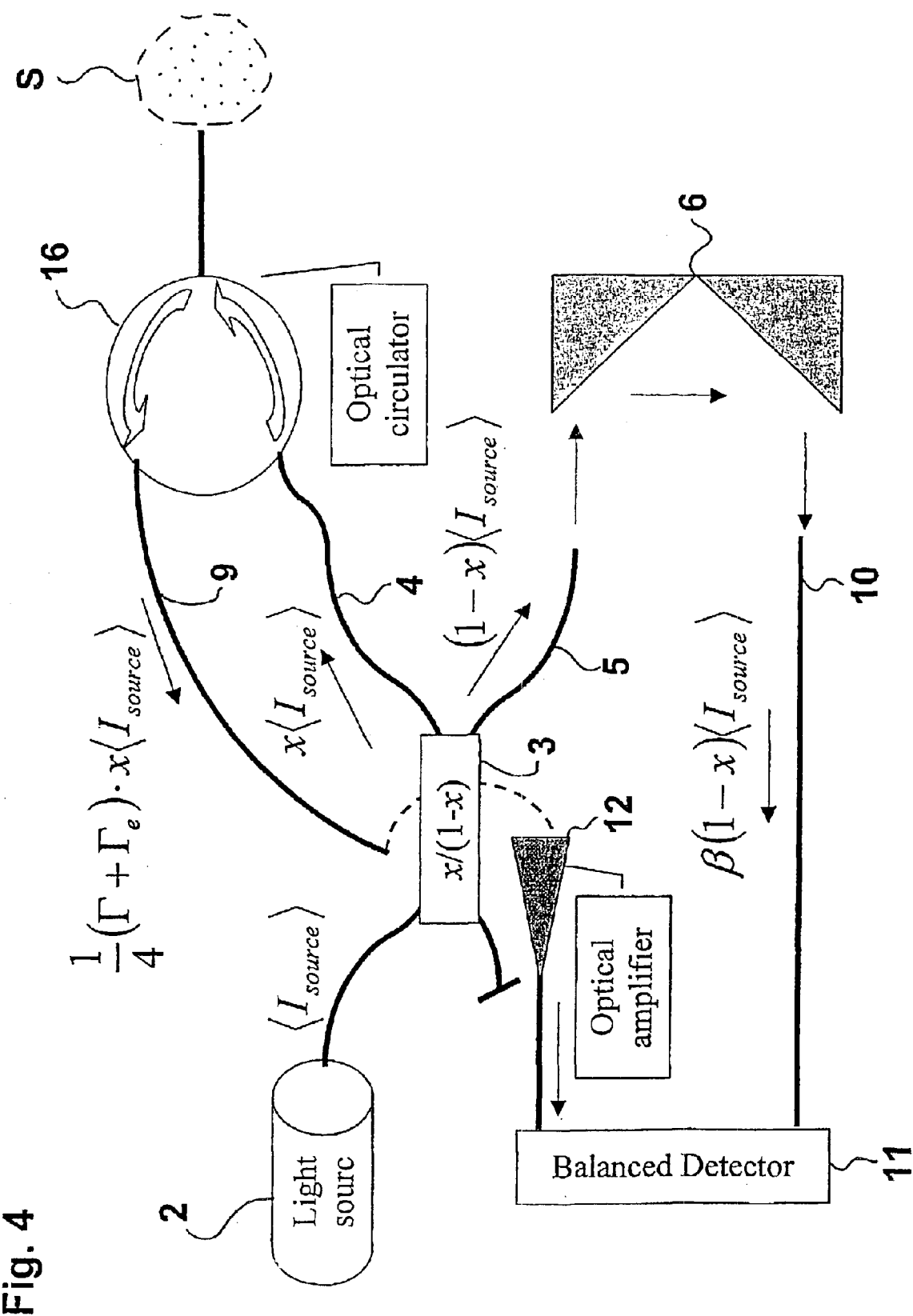

In FIG. 4, a refinement of the novel system in FIG. (2) is shown. To avoid the reduction of the first reflected light field 9 by the splitting means 3, an optical circulator 16 is inserted to direct substantially all the light power in the first reflected light field 9 to the optical amplifier 12.

Figure 5:
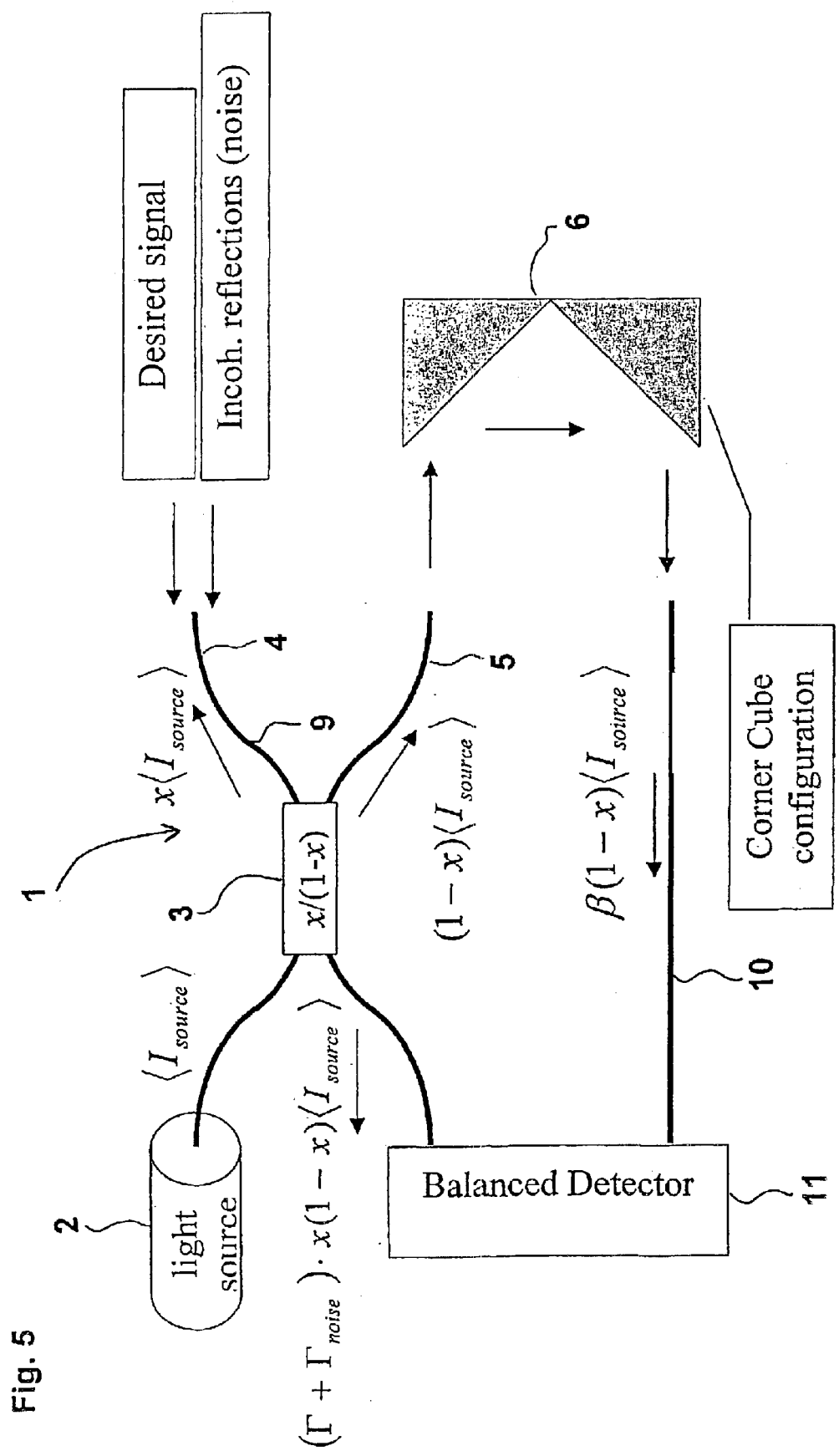

In FIG. 5 a reference system used for comparison reasons in the examples is shown. The reference system is according to prior art with no application implemented. The optical coherence system is denoted 1. A light source 2 provides a light signal that is directed to a splitting means 3 for dividing said light signal into a first light field 4 and a second light field 5. The splitting ratio may be set to any suitable ratio, exemplified by the ratio x/(1−x). The first reflected light field 8 is directed back to the splitting means 3. After the splitter, the first reflected light field 9 is—due to the nature of the splitter used—reduced by the factor (1−x) and directed to to the detection means 11 comprising a combining means. The second reflected light field 10 reflected from the reflection means 6 is also directed to the balanced detection means 11 comprising a combining means. The reflection means 6 is shown as a so-called corner cube configuration.

Figure 13:
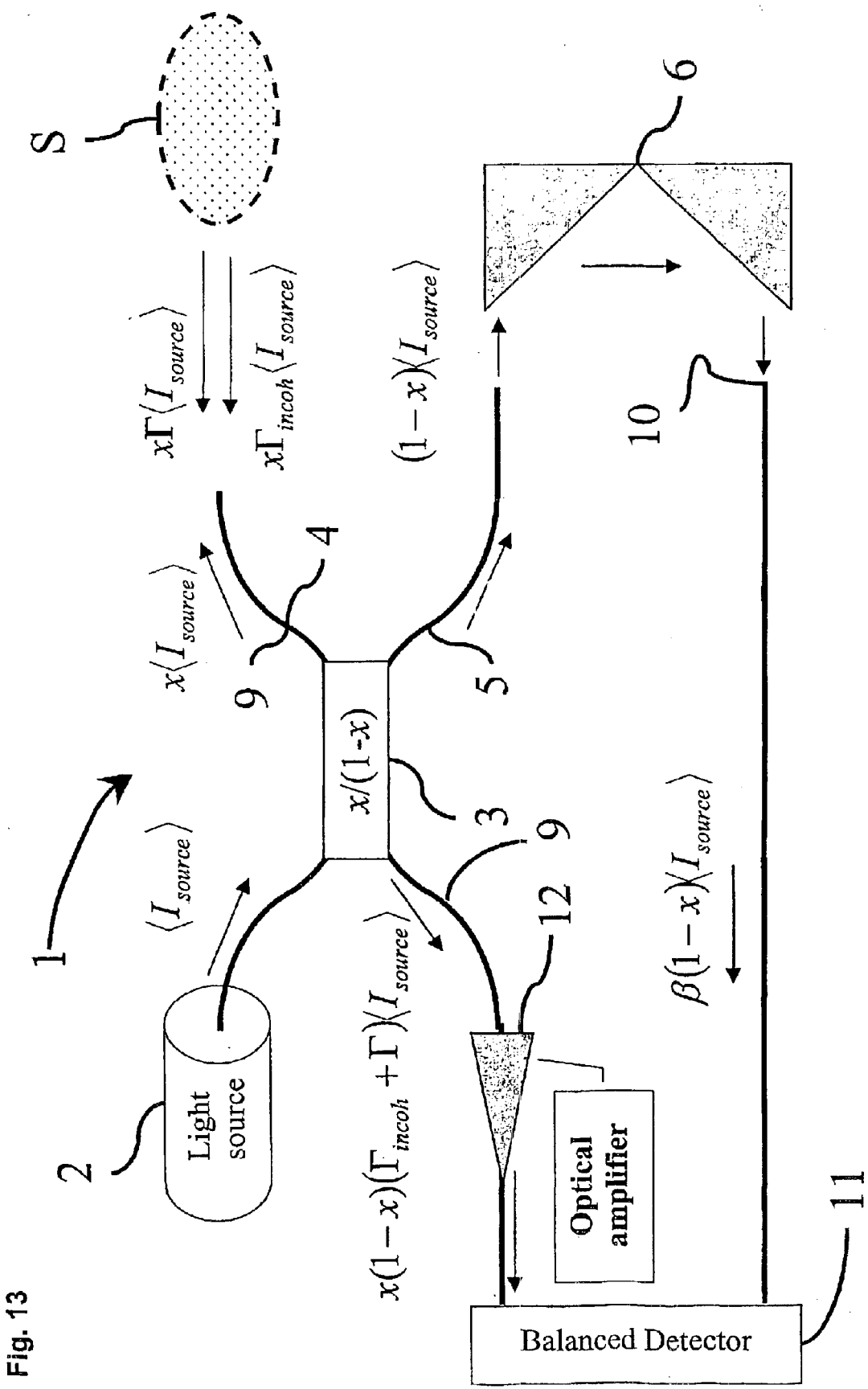
Figure 14:
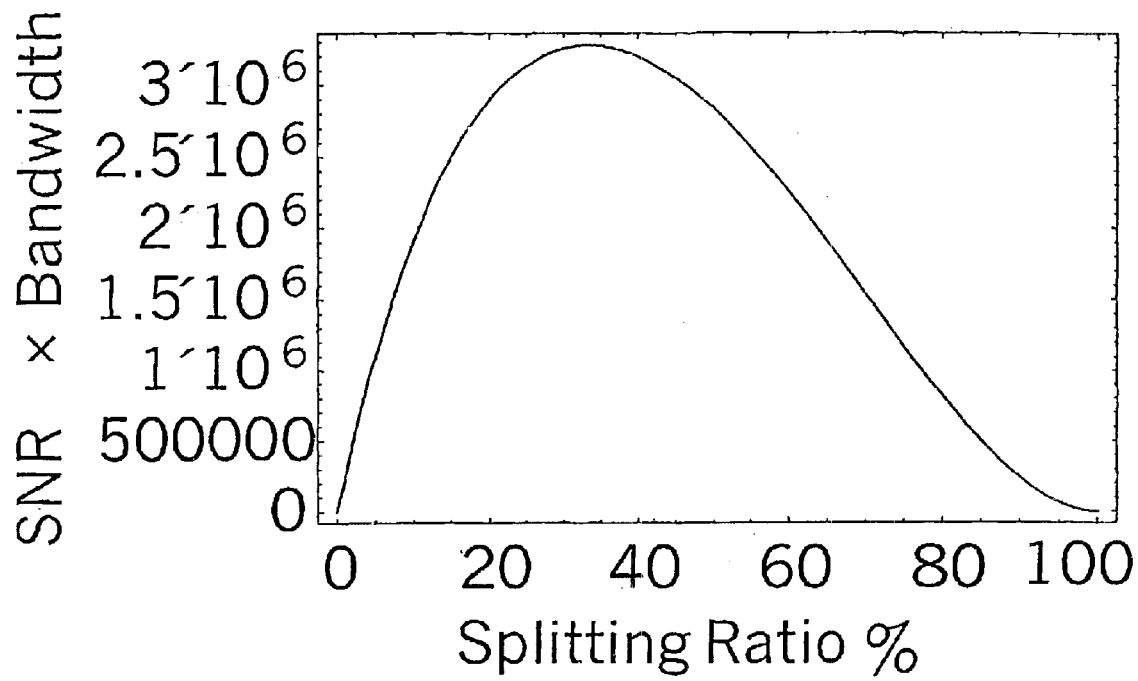
Figure 15:
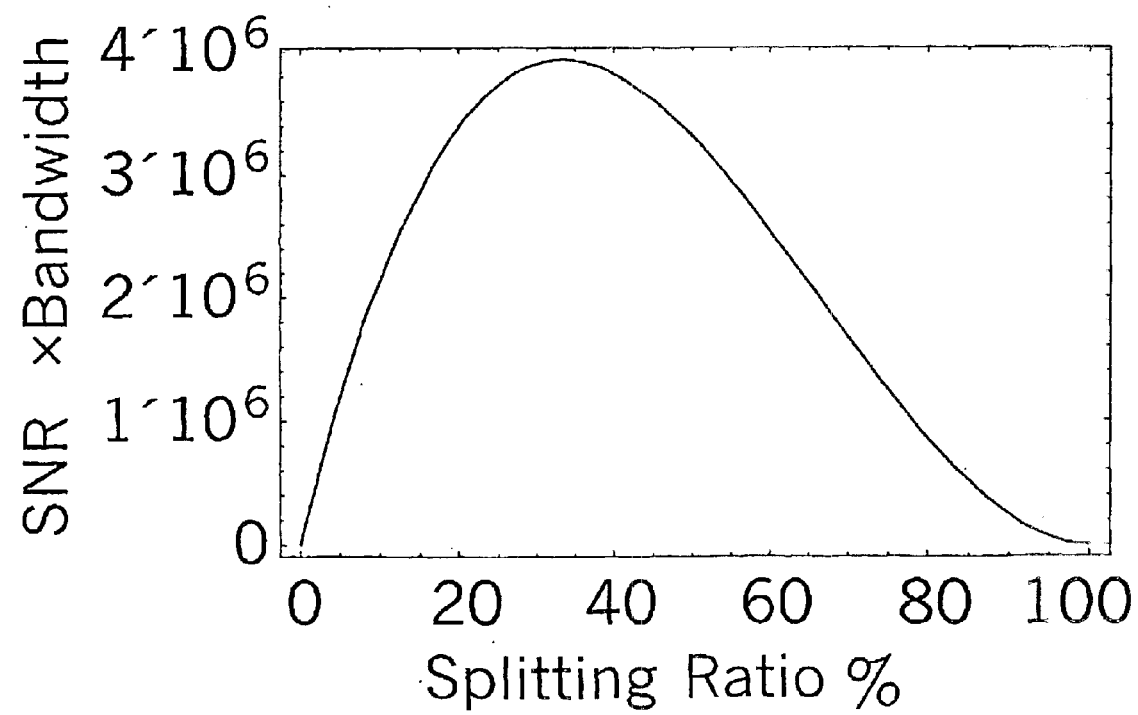
Figure 16:
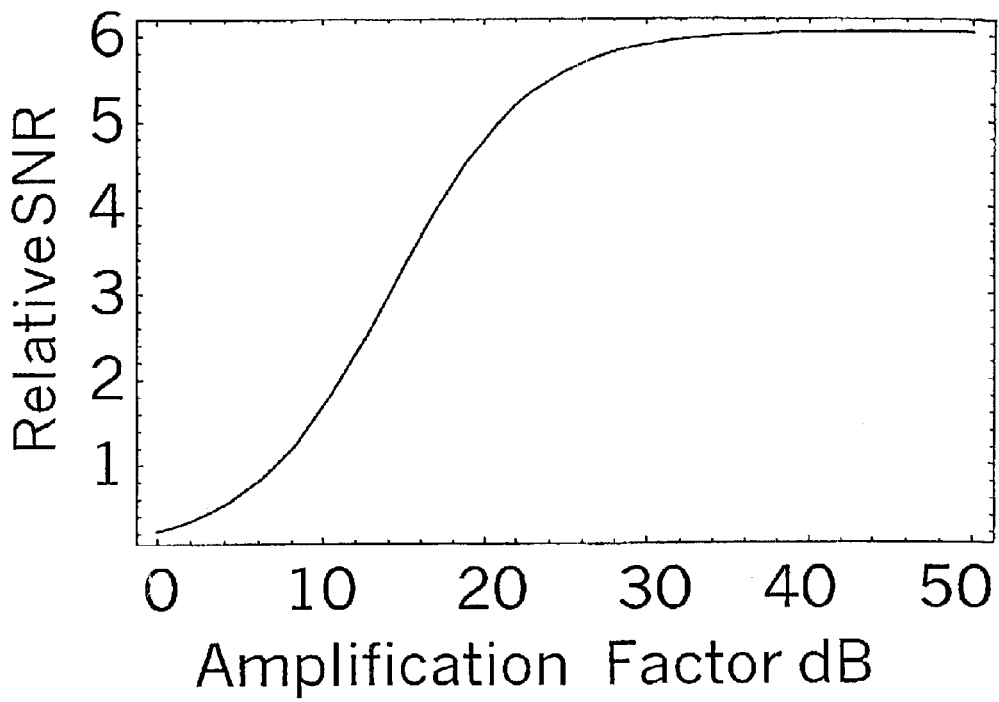
Figure 17:
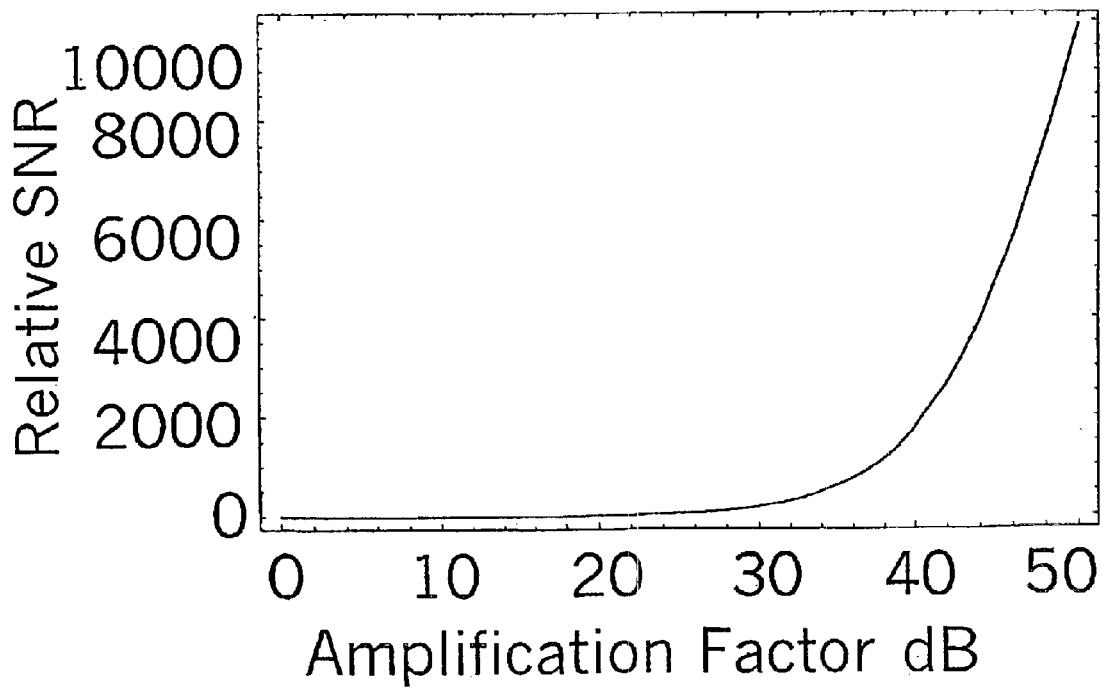
Figure 18:
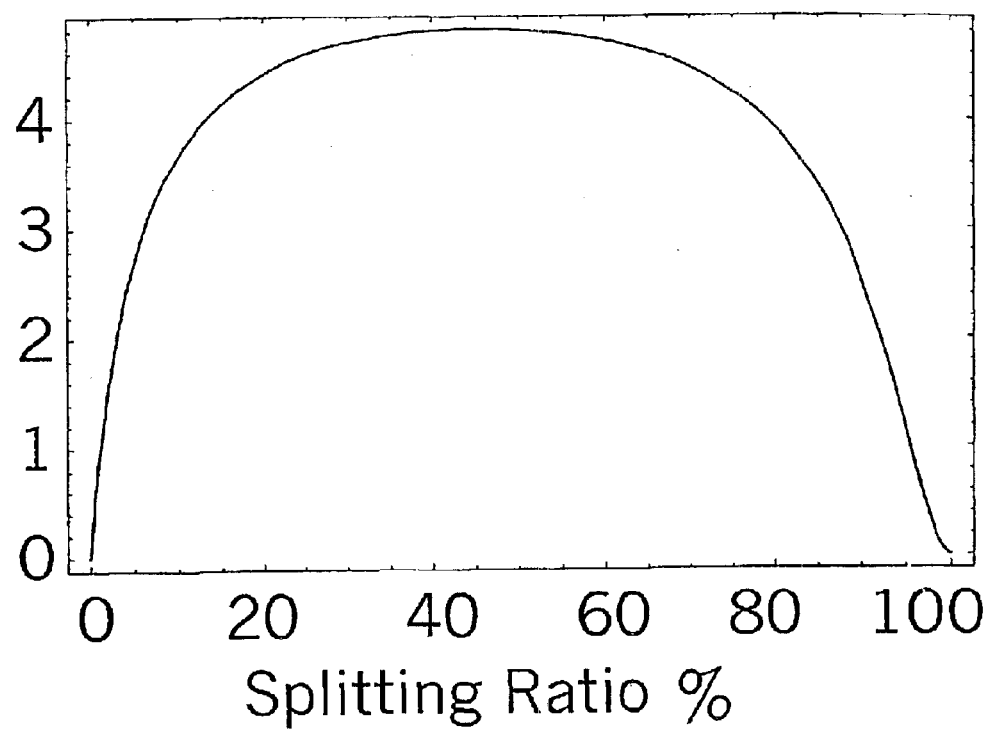
Figure 19:
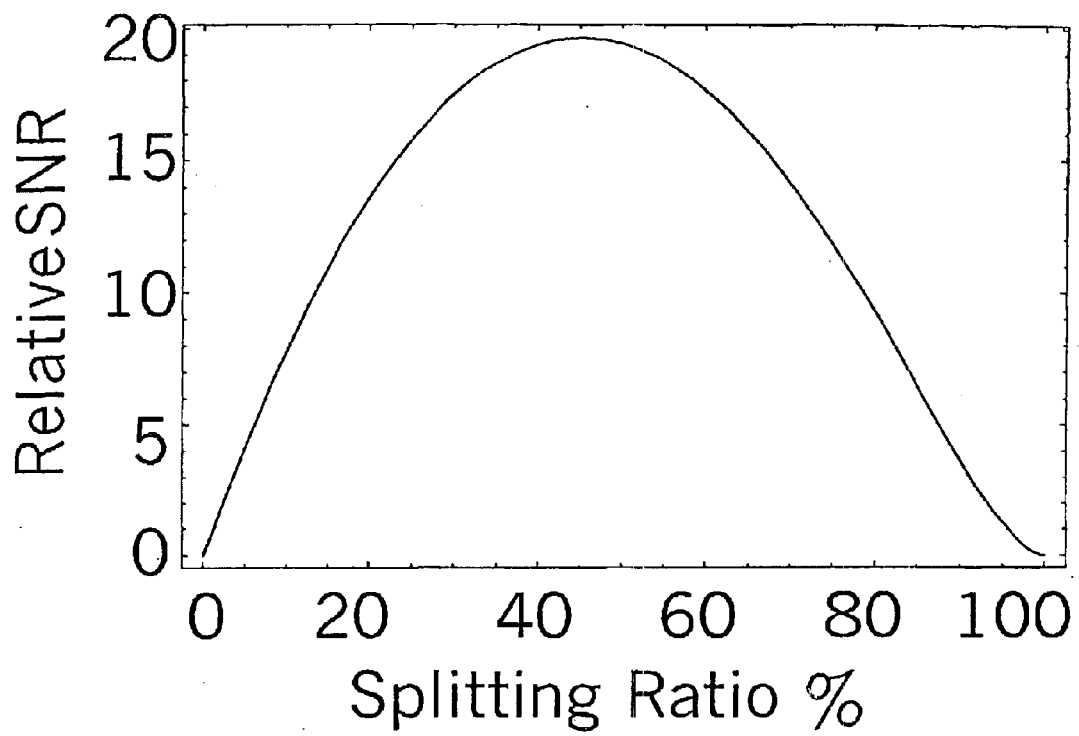
Figure 20:
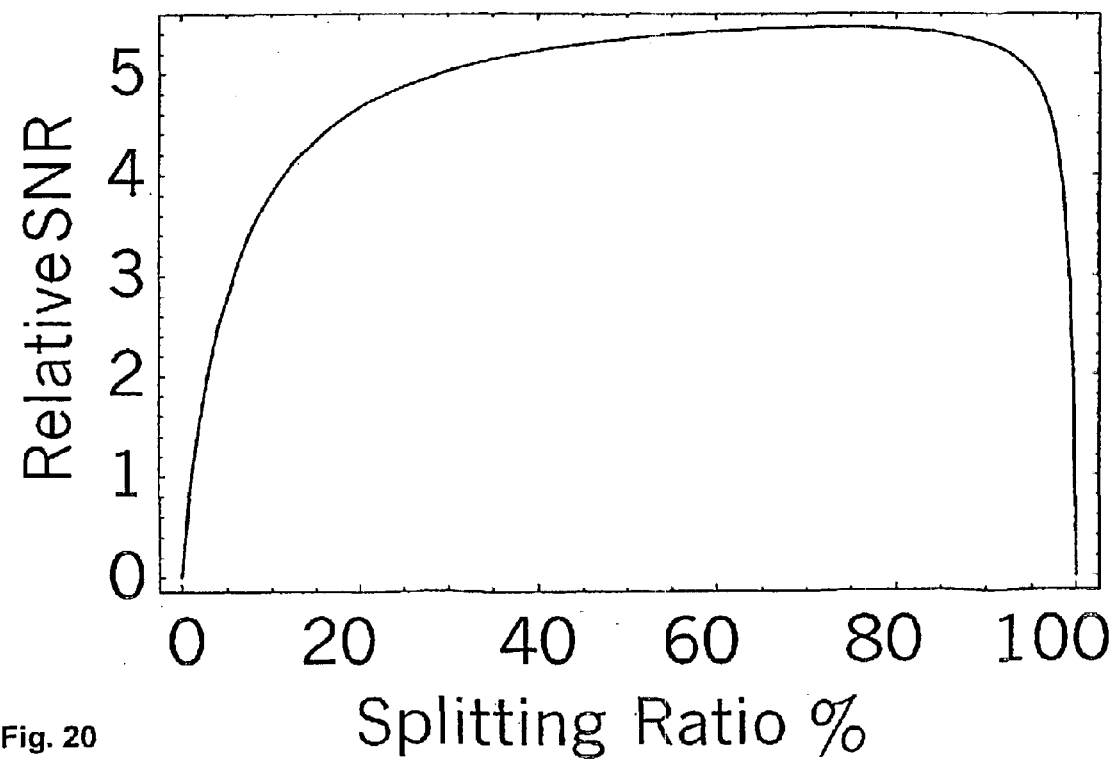
Figure 21:
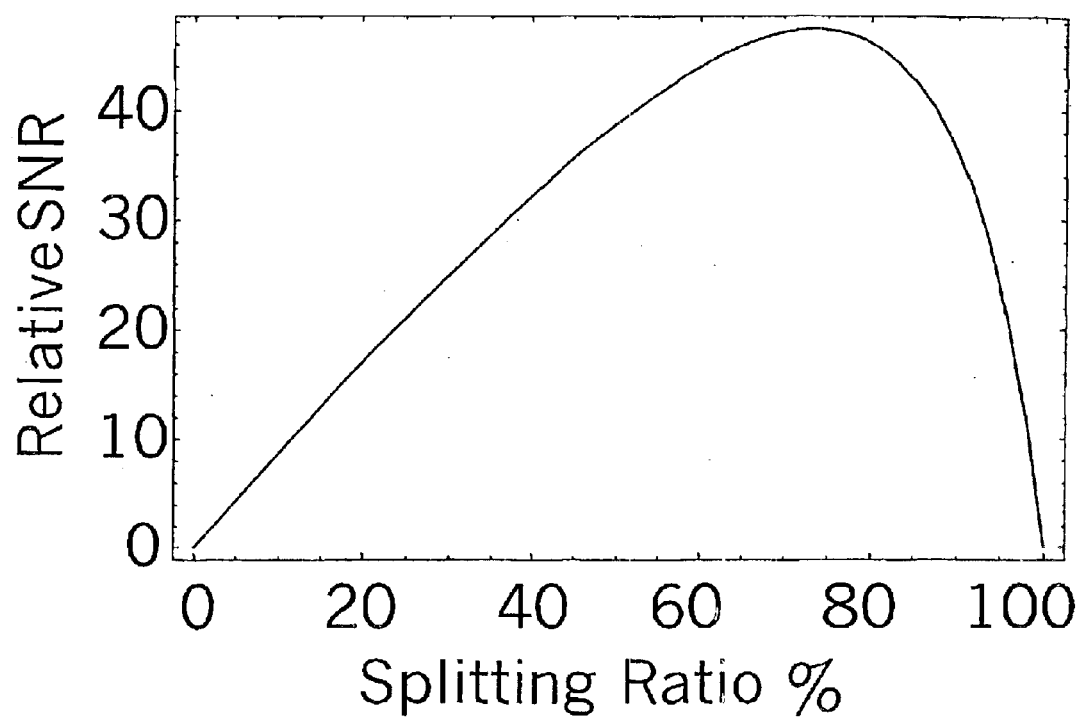

In FIG. 13 a detection scheme according to the invention is depicted. The optical coherence system is denoted 1. A light source 2 provides a light signal that is directed to a splitting means 3 for dividing said light signal into a first light field 4 and a second light field 5. The splitting ratio may be set to any suitable ratio, exemplified by the ratio x/(1−x). The first reflected light field 8 is directed back to the splitting means 3. After the splitter, the first reflected light field 9 is—due to the nature of the splitter used—reduced by the factor (1−x) and directed to the optical amplifier 12, and thereafter to the detection means 11 comprising a combining means. The second reflected light field 10 reflected from the reflection means 6 is also directed to the balanced detection means 11 comprising a combining means. The reflection means 6 is shown as a so-called corner cube configuration.

FIGS. 6-12 and 14-22 shows graphs relating to the examples below.

DETAILED DESCRIPTION

The present invention relates to an apparatus for optical coherence reflectometry, in particular optical coherence tomography.

One important aspect of the present invention is the route of the light field in the sample arm. The first reflected light field is amplified before being received by a combining means, said combining means being capable of receiving the first reflected light field from the sample arm as well as the second reflected light field from the reference arm. The amplified first reflected light field is directed to the combining means through another route than a route through the splitting means for dividing the light signal from the light source into the sample arm and the reference arm, respectively. Thereby, it is possible to direct substantially all light energy from the first reflected light field to the combining means, and to obtain fully the utilisation of the amplification of the first reflected light field. In other words by the present invention the amplified first reflected light field is directed to the combining means, so that only the reflected light field is amplified by the optical amplifier.

Another important aspect of the invention is that the optical amplifier inserted in the first reflected light field is different from the light source so that the effect of the light source may be regulated independent of the degree of amplification. In particular when using the apparatus in OCT certain safety regulations for the power density towards the sample has to be observed to reduce the risk of damages to the sample under examination, such as biological tissue.

Light Source

The light source should be a broad band source and may be chosen from one of the following categories:

continuous wave source, as for example superluminescent laser diodes or other white light sources, pulsed lasers, as for example femtosecond lasers, The shape of the spectrum is important because the signal received—from a single reflection—at the detector as the reference beam optical path length is varied is the autocorrelation of the source spectrum. Therefore, the wider the source spectrum the narrower signal is received as the reference beam optical path length is varied leading to a higher spatial resolution.

The wavelength of the light source is adjusted to the purpose of the analysis performed with the apparatus. The wavelength is mostly selected in the range from 500 nm to 2000 nm. For non-transparent solid tissue the wavelength is normally selected in the range from 1250 nm to 2000 nm.

For retinal examinations the wavelength is mostly selected in the range from 600 nm to 1100 nm.

Balanced/Unbalanced System

In general the system or apparatus according to the invention may be constructed as either an unbalanced system or a balanced system. The terms unbalanced and balanced are used in the normal meaning, ie. an unbalanced system refers to a system having one detecting means, whereas a balanced system refers to a system having two detecting means, wherein each detector receives signals from the sample arm as well as from the reference arm. In a balanced system the signals from the two detectors are subtracted from each other in order to obtain the result.

Also a double balanced system may be used in the apparatus according to the invention, a double balanced system referring to a system comprising four detecting means.

Noise

The noise in the apparatus or system according to the invention is the total sum of noise sources in the following parts:

Optical noise, such as noise from the light source and noise from the optical amplifier.

Receiver noise, such as thermal fluctuations in the electronic parts and shot noise.

The optical noise from the light source is manifested as the intensity noise relating to the first reflected light and intensity noise relating to the second reflected light as well as intensity noise from a mixture of both.

In the following calculations, a specific configuration for the balanced detection scheme applied to low coherent reflectometry has been chosen. However, the added benefit of introducing an optical amplifier with respect to the signal-to-noise-ratio also applies to other realizations of balanced detection and double balanced detection schemes.

For the following calculation a balanced detector system is assumed comprising of two detectors and a fiber-optic splitter as shown in FIG. 3.

The receiving device is assumed to receive three light fields, see FIG. 3: From the reference arm the field is $E_{reference}(t)$ having the intensity $I_{reference}$, from the reflection being measured the field is $E_{signal}(t)$ with intensity $I_{signal}$, and from the sum of all light, which does not have a matching pathlength with the reference and thus will not be temporally coherent with the reference, the field is $E_{Incoh}(t)$ with the intensity $I_{Incoh}$. Such light could stem from all reflections from the sample except the reflection being measured and from undesired reflections from fiber ends, lenses or other optical components or devices. Noise contributions from an optical amplifier may also be included in $I_{incoh}$.

Assuming that the coupler used in the balanced detector, see FIG. 3, is symmetric, the field incident on each detector 1 and detector 2 respectively can be written as $$\begin{bmatrix} E_1(t) \\ E_2(t) \end{bmatrix} = e^{i\varphi_r} \begin{bmatrix} a & be^{i\varphi} \\ be^{i\varphi} & a \end{bmatrix} \begin{bmatrix} E_{incoh}(t) + E_{signal}(t) \\ E_{reference}(t) \end{bmatrix}, \quad (1)$$

where $\varphi_r$ and $\varphi$ expresses phase changes due to the coupler, and a and b are coupling constants. It is known from the art that if the coupler is assumed lossless this constraint will mean that $a^2+b^2=1$ and $\varphi=\pm\pi/2$. For a 50/50 coupler $a=b=1/\sqrt{2}$. Thus for the balanced detector the incident fields are:

$$\begin{bmatrix} E_1(t) \\ E_2(t) \end{bmatrix} = \frac{1}{\sqrt{2}} \begin{bmatrix} 1 & e^{i\pi/2} \\ e^{i\pi/2} & 1 \end{bmatrix} \begin{bmatrix} E_{incoh}(t) + E_{signal}(t) \\ E_{reference}(t) \end{bmatrix}, \quad (2)$$

where $\varphi=\pi/2$ has been chosen and the common phase change $\varphi_r$ has been assumed zero without loss of generality. Using this it is straight forward to calculate the electrical current $i_1$ and $i_2$ in each detector due to a square law detection of the incident light power:

$$\begin{bmatrix} i_1(t) \\ i_2(t) \end{bmatrix} = \frac{1}{2}\eta\frac{e}{h\nu}\left\{\begin{bmatrix} I_{incoh}(t) + I_{signal}(t) + I_{reference}(t) \\ I_{incoh}(t) + I_{signal}(t) + I_{reference}(t) \end{bmatrix} + \begin{bmatrix} 2\text{Re}[E_{incoh}(t)E^*_{signal}(t) + E_{signal}(t)E^*_{reference}(t)e^{i\pi/2} + E_{incoh}(t)E^*_{reference}e^{i\pi/2}] \\ 2\text{Re}[E_{incoh}(t)E^*_{signal}(t) + E_{signal}(t)E^*_{reference}(t)e^{-i\pi/2} + E_{incoh}(t)E^*_{reference}e^{-i\pi}] \end{bmatrix}\right\}, \quad (3)$$

where $e$ is the electron charge, $h$ Planck's constant, $\nu$ the average wavelength of the light source, $\eta$ the quantum efficiency of the photodetectors, and Re[ ] denotes taking the real part of the argument inside the brackets. Since the balanced detector detects the difference between the two currents, the received electrical signal $i(t)$ becomes:

$$i(t) = \qquad (4)$$
$$i_1(t) - i_2(t) = \eta\frac{e}{h\nu}2\text{Re}[iE_{signal}(t)E^*_{reference}(t) + iE_{incoh}(t)E^*_{reference}(t)]$$

The first term is the signal due to the reflection to be measured and the second term gives rise to the so-called beat noise which was studied by K. Takada ("Noise in Optical Low-Coherence Reflectometry") IEEE J. of Quant. Electronics JQE-34 (7), 1098 (1998)).

The noise contributions are all expressed as the received noise power after electrical subtraction of the two signals received by each photodetector, measured per unit bandwidth of the receiving circuit.

Takada found that the beat-noise received, due to $I_{incoh}$ in the absence of an optical amplifier is given by:

$$\langle\Delta i^2_{beat}\rangle = \left(\eta\frac{e}{h\nu}\right)^2\frac{2}{\delta_\nu}\langle I_{reference}\rangle\langle I_{incoh}\rangle, \quad (5)$$

where $\delta\nu$ [Hz] is the effective line-width of the light source used. To simplify the following calculations we assume that the optical amplifier imposes no spectral distortion on the first reflected light field and that the bandwidth of the optical amplifier is identical to that of the light source.

It is common knowledge within the art that the so-called shot-noise due to the particle nature of the photon-to-electron conversion in the photodetectors is given by $$\langle \Delta i_{shot}^2 \rangle = 2e\left(\eta \frac{e}{h\nu}\right)(\langle I_{signal} \rangle + \langle I_{reference} \rangle + \langle I_{incoh} \rangle). \quad (6)$$

The photodetectors also have an inherent noise contribution, which is independent of the incident light power. There are two contributions to this noise: Thermal noise in the electrical circuit of the detectors and shot-noise due to dark current in photodetector. The reciever noise is:

$$\langle \Delta i_{reciever}^2 \rangle = \langle \Delta i_{thermal}^2 \rangle + \langle \Delta i_{dark}^2 \rangle = 2\left(\frac{4k_B T}{R} F_n + 2e\langle i_{dark} \rangle\right), \quad (7)$$

where $k_B$ is Boltzman's constant, R the load resistance of each of the detectors, T the temperature, $F_n$ the noise figure of the electrical circuit of the detectors normally dominated by the preamplifier, ($i_{dark}$) the dark current in each detector and the factor of 2 is due to having two independent detectors. However, this receiver noise, independent of the incident light, is often more conveniently measured experimentally.

Thermal fluctuations in the electronic parts are independent of the amount of light used, and furthermore, the thermal fluctuations may be reduced by cooling of the detectors, and also by optimising the construction.

Shot noise relates to the particle nature of the light. The shot noise is proportional to the amount of light received.

When inserting an optical amplifier in the apparatus it is inherent that in addition to the amplification of the signal desired the optical noise will inevitably also be amplified.

In this calculation an optical amplifier is modelled to amplify the incoming light and add optical noise due to intrinsic amplifier noise. Hence, the light intensity emitted from an optical amplifier is given by $$\langle I_{out} \rangle = \chi \langle I_{in} \rangle + \langle I_{noise} \rangle, \quad (8)$$

where $\chi$ is the amplification factor, $I_{in}$ the intensity of the incident light, and $I_{noise}$ the intensity due to the intrinsic amplifier noise. For simplicity it is assumed that the optical bandwidth of $I_{noise}$ equals that of the light source of the system, and that all wavelengths of $I_{in}$ is amplified by the same factor.

Assuming that the pathlength of the reference light is perfectly matched to that of the signal light being reflected by the reflection to be measured, the signal power received by the balanced detector is given by $$\langle i_{signal}^2 \rangle = \left(\eta \frac{e}{h\nu}\right)^2 \langle I_{reference} \rangle \langle I_{signal} \rangle, \quad (9)$$

where it is assumed that the source is unpolarized. If polarized light is used and the reference and signal light is made to match exactly, the signal power $i^2_{signal}$ signal in Eq. (9) should be multiplied by a factor 2.

Using the above equations it is straight forward to derive the signal-to-noise ratio (SNR):

$$SNR = \frac{\langle i_{signal}^2 \rangle}{B(\langle \Delta i_{reciever}^2 \rangle \langle \Delta i_{shot}^2 \rangle \langle \Delta i_{beat}^2 \rangle)} \quad (10)$$

$$= \frac{\alpha^2 \langle I_{reference} \rangle \langle I_{signal} \rangle}{B[\langle \Delta i_{reciever}^2 \rangle + 2e\alpha(\langle I_{signal} \rangle + \langle I_{reference} \rangle + \langle I_{incoh} \rangle) + 2\alpha^2/\delta_\nu \langle I_{reference} \rangle \langle I_{incoh} \rangle]},$$

where B is the effective bandwidth of the electrical detector system, and $\alpha = \eta e/h\nu$ the responsivity of the detector.

Below the individual terms in Eq. (10) according to the configuration in FIG. (2) are specified.

If the light source emits the light intensity ($I_{source}$) then the light intensity towards the receiver from the reference will be $$\langle I_{reference} \rangle = (1-x)\beta \langle I_{source} \rangle, \quad (11)$$

where X is the coupling ratio towards the sample of the first coupler from the source, and $\beta$ is a factor describing the loss of power as the light is coupled out of the fiber, reflected (in this case from a movable retroreflector), and coupled back into the fiber. For simplicity, and without loss of generality, the factor $\beta$ is set to unity.

For the equations mentioned below the equations 12'–16' related to a system of FIG. 2 and 12–16 relate to a system of FIG. 13. Thus, in a first embodiment the light power incident upon the optical amplifier is $$\langle I_{in} \rangle = x(1-x)(\Gamma + \Gamma_{incoh}) \langle I_{source} \rangle \quad (12)$$

where $\Gamma$ is the reflectivity of the reflection to be measured, and $\Gamma_{incoh}$ the sum of all other reflectivites from the sample and from e.g. a collimating or focusing lens guiding the light from the fiber to sample and back into the fiber. Note that the each individual reflectivity should be reduced by the applicable coupling loss to and from the fiber. The light power incident on the balanced detector from the optical amplifier will then be $$\langle I_{out} \rangle = \chi x(1-x)(\Gamma + \Gamma_{incoh}) \langle I_{source} \rangle + \langle I_{noise} \rangle \quad (13)$$

Thus the light power incoherent to the reference becomes $$\langle I_{incoh} \rangle = \chi x(1-x)\Gamma_{incoh} \langle I_{source} \rangle + \langle I_{noise} \rangle \quad (14)$$

and the light power related to the desired signal due to the reflectivity $\Gamma$ becomes $$\langle I_{signal} \rangle = \chi x(1-x)\Gamma \langle I_{source} \rangle \quad (15)$$

Inserting Eq. (11), Eq.(14) and Eq.(15) into Eq (10) yields $$SNR = \frac{\alpha^2 \chi x(1-x)^2 \Gamma}{B\left[\frac{\langle \Delta i^2_{receiver}\rangle}{\langle I_{source}\rangle^2} + 2e\alpha\left(\frac{(1-x)(1+\chi x(\Gamma + \Gamma_{incoh}))}{\langle I_{source}\rangle} + \frac{\langle I_{noise}\rangle}{\langle I_{source}\rangle^2}\right) + \frac{2\alpha^2}{\delta_v}\left(\chi x(1-x)^2 \Gamma_{incoh} + \frac{\langle I_{noise}\rangle}{\langle I_{source}\rangle}\right)\right]} \quad (16)$$

In another embodiment the light power incident upon the optical amplifier is $$\langle I_{in}\rangle = \frac{1}{4}x(\Gamma + \Gamma_{incoh})\langle I_{source}\rangle, \quad (12')$$

where $\Gamma$ is the reflectivity of the reflection to be measured, and $\Gamma_{Incoh}$ the sum of all other reflectivites from the sample and from e.g. a collimating or focusing lens guiding the light from the fiber to sample and back into the fiber. Note that the each individual reflectivity should be reduced by the applicable coupling loss to and from the fiber. The light power incident on the balanced detector from the optical amplifier will then be $$\langle I_{out}\rangle = \chi \frac{1}{4}x(\Gamma + \Gamma_{incoh})\langle I_{source}\rangle. \quad (13')$$

Thus the light power incoherent to the reference becomes $$\langle I_{incoh}\rangle = \chi \frac{1}{4}x\Gamma_{incoh}\langle I_{source}\rangle + \langle I_{noise}\rangle. \quad (14')$$

and the light power related to the desired signal due to the reflectivity $\Gamma$ becomes $$\langle I_{signal}\rangle = \chi \frac{1}{4}x\Gamma\langle I_{source}\rangle. \quad (15')$$

Inserting Eq. (11), Eq.(14) and Eq.(15) into Eq (10) yields

However the present inventors have found due to the location of the amplifier as well as the route of the first reflected light field that a further increase in SNR may be obtained when using a changeable splitting ratio, so that from 1% to 99% of the light energy from the light source is directed to the sample arm. It is preferred that more than 50% of the light energy is directed to the sample, such as from 50% to 99% of the light energy from the light source is directed to the sample arm, such as from 55% to 90% of the light energy from the light source is directed to the sample arm, such as from 60% to 85% of the light energy from the light source is directed to the sample arm, such as from 65% to 85% of the light energy from the light source is directed to the sample arm.

In another embodiment it is preferred that from 1% to 60% of the light energy from the light source is directed to the sample arm, such as from 20% to 55% of the light energy from the light source is directed to the sample arm, such as from 30% to 50% of the light energy from the light source is directed to the sample arm, such as from 40% to 50% of the light energy from the light source is directed to the sample arm.

Sample Arm—First Light Field Route

The apparatus according to the invention comprises means for directing the first light field to the sample. In a preferred embodiment at least a part of the means for directing the first light field to the sample comprises an optical fibre, so that the means in total comprises an optical fibre and an optical system. An optical system may be included for focusing the first light field to the sample. The optical system for example being one or more lenses.

It is preferred that the first light field is directed to the sample without being amplified. Thereby the intensity of the $$SNR = \frac{\frac{1}{4}(1-x)\chi x \Gamma}{B\left[\frac{\langle \Delta i^2_{reclever}\rangle + 2e\alpha\langle I_{noise}\rangle}{\alpha^2 \langle I_{source}\rangle^2} + \frac{1}{2}e\frac{\chi x(\Gamma + \Gamma_{incoh}) + 4(1-x)(1+\alpha/e\delta_v\langle I_{noise}\rangle)}{\alpha\langle I_{source}\rangle} + \frac{1}{2\delta_v}(1-x)x\chi\Gamma_{incoh}\right]} \quad (16')$$

In analogy with this derivation, the SNR can be derived for a wide variety of low-coherent reflectometer systems with balanced detection and thus the performance of such systems can be easily compared.

Splitting Means

The general principle of OLCR and OCT is that distance travelled by the light in the sample arm is correlated to the distance travelled by the light in reference arm.

The light is emitted from a light source as discussed above and divided into a first light field and a second light field by a splitting means. The splitting means may be any means suitable for splitting a light signal into two light fields. The splitting means may be selected from a bulk optic splitting means, a fibre optic splitting means, a holographic optical element or a diffractive optical element.

In one embodiment the apparatus according to the invention comprises a splitting means capable of dividing the light signal into the sample arm and the reference arm with a splitting ratio of the splitting means being substantially 50%/50%.

first light field onto the sample is exclusively determined by the light source. This leads to a better control of the light intensity in the sample arm, since the light directed to the sample conforms to the practical limits for sample light, such as an upper limit for the intensity to avoid damages to the sample, and the light reflected from the sample may be amplified to the degree necessary for the SNR to be suitably increased. Thus, the amplifier is preferably located in a part of the sample arm by which only the reflected light field is traveling. This may be accomplished by inserting a splitting means or a circulator to receive the reflected first light field from the sample, or by inserting the optical amplifier after the first reflected light field has passed the splitting means used to split the light into the first and second light fields.

In a preferred embodiment a circulator is inserted whereby substantially all light energy reflected from the sample is directed as the first reflected light field to the optical amplifier.

The term light field as used herein means light field as normally used for the light in optical fibres, but does also include a light beam as normally used in bulk systems and in the optical system.

Scanning Head

The sample is scanned by means known in the art, such as galvanometer scanners, polygon mirrors, resonant scanners, a scanning head.

Amplifier

Any optical amplifier suitable for amplifying the reflected first light field may be interposed in the light route from the sample to the combining means. The amplifier may thus be a semiconductor, a resonant amplifier or a fibre and/or Raman amplifier. The amplification factor may be in the range from 1.5 to 1,000,000 times, such as from 20 to 500,000 times, for example from 20 to 100,000 times, such as from 20 to 50,000 times, such as from 20 to 10,000 times, such as from 20 to 1000 times, such as from 20 to 100 times.

Reference Arm—Second Light Route

The apparatus according to the invention also comprises means for directing the second light field to the reflecting means. In a preferred embodiment at least a part of the means for directing the second light field to the reflecting means comprises an optical fibre, so that the directing means in total comprises an optical fibre and an optical system. The optical system may be used for directing the second light field to the reflecting means, such as any kind of lenses, gratings etc., known to the person skilled in the art.

Attenuation of the reflected second light field may be useful when using an unbalanced system, whereas attenuation of the reference arm does not add anything further to the SNR in a balanced system.

In a preferred embodiment the reflected second light field does not pass the splitting means for dividing the light signal when travelling towards the combining means. It is an advantage to maintain as much as possible of the second reflected light field on the route to the combining means. This may be accomplished by inserting a circulator to receive the second reflected light field from the reflection means to direct the second reflected light field directly to the combining means.

In a preferred embodiment a circulator is inserted to receive the second reflected light field whereby substantially all light energy reflected from the reflecting means is directed as the second reflected light field to the combining means.

The reflecting means may be any means suitable for reflecting the light in the reference arm or means having a similar function, the function of the reference arm being its capability of allowing light to travel any distance identical to the distance travelled by the light in the sample arm. The reflecting means may be a mirror or another structure having reflective properties. An example may be a mirror mounted on a high precision sledge system optionally including a piezo-electric element capable of vibrating, whereby for one position of the sledge a point may be sampled many times.

Also the reflecting means may be means allowing variation of the optical path-length, such as a rotating mirror in the reference arm directing the light field to a reflecting grating. As the mirror rotates the distance to the grating changes and with this the optical path-length.

The length of the reference arm may be modulated by using a piezo-electric fibre stretcher, methods based on varying the path length of the reference arm light be passing the light through rapidly rotating cubes or other rotating optical elements, and methods based on Fourier-domain pulse-shaping technology which modulate the group delay of the reference arm light by using an angularly scanning mirror to impose a frequency-dependent phase on the reference arm light after having been spectral dispersed as discussed in U.S. Pat. No. 6,002,480 which is hereby incorporated by reference.

In order to simulate the distance travelled by the light in the sample, the optical length of the reference path is preferably altered, and the apparatus according to the invention comprises means for altering the optical length. The means for altering the optical path length may be an optical modulator, for example an electro-optic modulator or a fibre stretcher.

Combining Means

The combining means is any suitable means capable of receiving two light fields and combining the light fields into at least one light signal. In a preferred embodiment the combining means is a coupler.

Detecting Means

The system comprises conventional detecting means. The detecting means is essentially a photodetector chosen accordingly to match the source wavelength, a combination of photodetectors arranged to make up a balanced scheme, or a combination of photodetectors arranged to make up a double-balanced scheme.

Furthermore, the detecting means may be a linear array of photodetectors without or combined with a dispersive element arranged so that the array provides depth and spectral information. The detecting means may also be a linear charge-coupled device (CCD) array without or combined with a dispersive element arranged so that the array provides depth and spectral information.

Finally, the detecting means may be a two-dimensional array of photodetectors without or combined with a dispersive element arranged so that the array provides depth and spectral information. The detecting means may also be a two-dimensional CCD array without or combined with a dispersive element arranged so that the array provides depth and spectral information. For example, the dispersive element may be a diffraction grating (reflection or transmission), a prism or a combination of prisms.

End Reflections

In a preferred embodiment the SNR is further increased by reducing non-sample reflections, such as the fibre end reflections in the sample arm. By reducing the non-sample reflections in combination with amplification of the first light field an increase of the relative SNR is increased up to about 20 dB, such as about 17 dB. It has been shown that the amplification of the light field in the sample arm is improved additionally when reducing reflections.

The end reflections may be reduced by anti-reflex coating the fibre ends of the fibres in one or both of the arms.

Also the fibre ends may be cleaved at an angle to reduce reflections, such an angle being at least 5 degrees, such as preferably at least 7 degrees.

The anti-reflex coating and the cleaving of the fibre ends may be used as alternatives or in combination.

Processing/Displaying

The result obtained may be further processed to obtain relevant information based on the detection signal relating to the distance/coherence. In one embodiment the detection signal is sent to a computer for analysis. Depending on the object scanned, the computer may provide an image relating to for example the tissue scanned.

In relation to detection of inhomogeneities in for example optical waveguides, the computer may provide information relating to the distance to the inhomogeity and for example also an image of the inhomogeneity.

The result may be sent from the computer to a display and/or a printer and/or stored in a storage means.

Penetration Depth

The parameters that govern OCT performance are longitudinal and transverse resolution, dynamic range, measurement speed, and the centre wavelength of the light source.

The depth to which an illumination field of light penetrates within turbid media, such biological tissue or the like, is determined by the amount of scattering and absorption present in the media.

In tissue scattering diminishes rapidly with increasing wavelength throughout the visible and infrared wavelength regions. Absorption in tissue is dominated by resonant absorption features, and no simple scaling can be assumed. For near-infrared light (~0.8 μm), where absorption is relatively week, scattering is the dominant mechanism of attenuation. At longer wavelengths, such as 1.3 μm, 1.55 μm or 1.9 μm, scattering is minimal, and water absorption becomes increasingly important.

The longitudinal resolution governed by the coherence length is inversely proportional to the optical bandwidth of the light source.

By the present invention the penetration depths may be increased or even doubled due to the increased SNR depending on the optical properties of the medium.

The transversal resolution is essentially given by the well-known diffraction limit, i.e. the minimum focal spot, which is the resolving power. The diffraction limit is determined by the wavelength, the effective aperture of the beam and the focal length of the lens as known from the art.

The measurement speed, i.e. the time to perform a single a-scan and capture the interference signal, may be defined in different ways, and therefore a unique measure for this quantity cannot be given. However, increasing the scan speed implies increasing the electrical bandwidth of the detecting means and this may ultimately lead to an increase of the receiver noise. As shown by our analysis above, the introduction of the optical amplifier amplifying the reflected light from the sample may be even more advantageous if the noise in the detecting means increases. In other words, the optical amplifier may to a certain extent aid to overcome receiver noise.

Thus, due to the amplification system according to the present invention it is possible to conduct a faster scanning than with state of the art systems.

Transverse Scanning

The light path preferably includes a transverse scanning mechanism for scanning the probe beam within the sample, for example an actuator for moving the apparatus in a direction substantially perpendicular to the sample. Such a scanning mechanism can have a micro-machined scanning mirror. A longitudinal scanning mechanism can also be provided to scan in a direction parallel to the probe beam. Scanning allows the apparatus to create images. Longitudinal scanning in the direction of the probe beam axis, along with scanning in a direction perpendicular to the axis, provides the possibility of obtaining an image of a vertical cross section of the sample.

It is of course understood that although it is preferred to scan the sample apparatus in relation to the sample, the sample may also be scanned with respect to a stationary sample probe or a combination of these.

Applications

The apparatus and method according to the present invention may be used in any application normally applying OCT scanning as well new technical fields wherein the increased SNR allows the use of the present apparatus. Thus, the apparatus may be used for so-called optical biopsies, wherein a segment of tissue, such as the skin, mucosa or any other solid tissue is examined by OCT to diagnose any cellular abnormalities, such as cancer or cancer in situ. Furthermore, any malignant growth may be detected by the present apparatus.

Due to the optical amplification conducted as discussed herein it is possible to increase the relative SNR, for example 10 dB, such as about 15 dB, drastically increasing the penetration depth of the system. Thus, above malignacies in the skin or mucosa may be detected directly by using the present invention. Furthermore, the apparatus may be coupled to catheters or the like to scan internal body parts, such as the gastro-intestinal tract, a vessel or the heart or any body cavity. Also, the apparatus may be used for scanning during a surgical operation.

Also, the present apparatus has improved the use of OCT in ophtalmical application due to the increased penetration depth, such as in corneal topography measurements and as an aid in ophtalmical surgery, for example for focusing on the posterior intraocular lens capsule for use in cataract surgery.

The present invention may also be applied in convention OLCR applications, such as detection or imaging of inhomogeneities in optical waveguides or devices, i.e. wherein the sample is an optical waveguide or an integrated optical device. In another embodiment the sample may be a polymer. In yet another embodiment the sample may be a silicon-based integrated circuit.

EXAMPLES

Here follows a comparison of an OCT system according to prior art and two different OCT systems according to the present invention exemplifying the added benefit of introducing an optical amplifier. The effect of using a system where all reflections contributing to $I_{incoh}$ has been reduced as much as possible e.g. through coating of all surfaces, as well as the effect of changing the splitting ratio on the splitter from the source, is demonstrated. The former case in which all surfaces are coated is reffered to as the coated case, whereas not coating the surfaces is referred to as the uncoated case.

The system parameters used are $$\langle I_{source} \rangle = 10 \text{ mW},$$

$$\langle I_{noise} \rangle = 2 \text{ mW},$$

$$B = 10 \text{ kHz},$$

$$\Gamma = r_b \exp(-\mu_t z) = 0.4\% \exp(-5 \text{ mm}^{-1} \cdot 2 \text{ mm}),$$

$$\Gamma_{noise} = \begin{cases} 0.04, \text{ uncoated case} \\ 10^{-5}, \text{ coated case} \end{cases},$$

$$\langle \Delta i^2_{receiver} \rangle = -115 \text{ dBm/Hz},$$

$$\alpha = 0.9 \text{ A/W}$$

$$\delta_v = c(1/\lambda_{min} - 1/\lambda_{max}) = c(1/1285 \text{ nm} - 1/1335 \text{ nm}) = 8.7 \text{ THz}$$

where the c is the speed of light in vacuum. The light source is chosen to have a center wavelength of 1310 nm and a spectral bandwidth of 50 nm Here a damping coefficient $\mu_t$=5 mm$^{-1}$, a probing depth z=2 mm, and a reflection coefficient within the sample of 4% have been chosen. It should be noted that more evolved and accurate methods to estimate r based on the chosen parameters do exist in the art. However, for the purpose of system performance evaluation, a rough estimate is sufficient to assign $\Gamma$ a practical value.

Example 1a
a) Choice of Reference System

First, a reference system against which to compare the performance is decided. This system can be seen in FIG. 5. Through a similar analysis as to the one used to derive Eq. 16', the SNR of the reference system may be found. By doing so, it is found that the optimum splitting ratio toward the sample is approximately 35% and 65% towards the reference both for a system with and without coated surfaces. A system with this splitting ratio is chosen as reference system.

Figure 1:
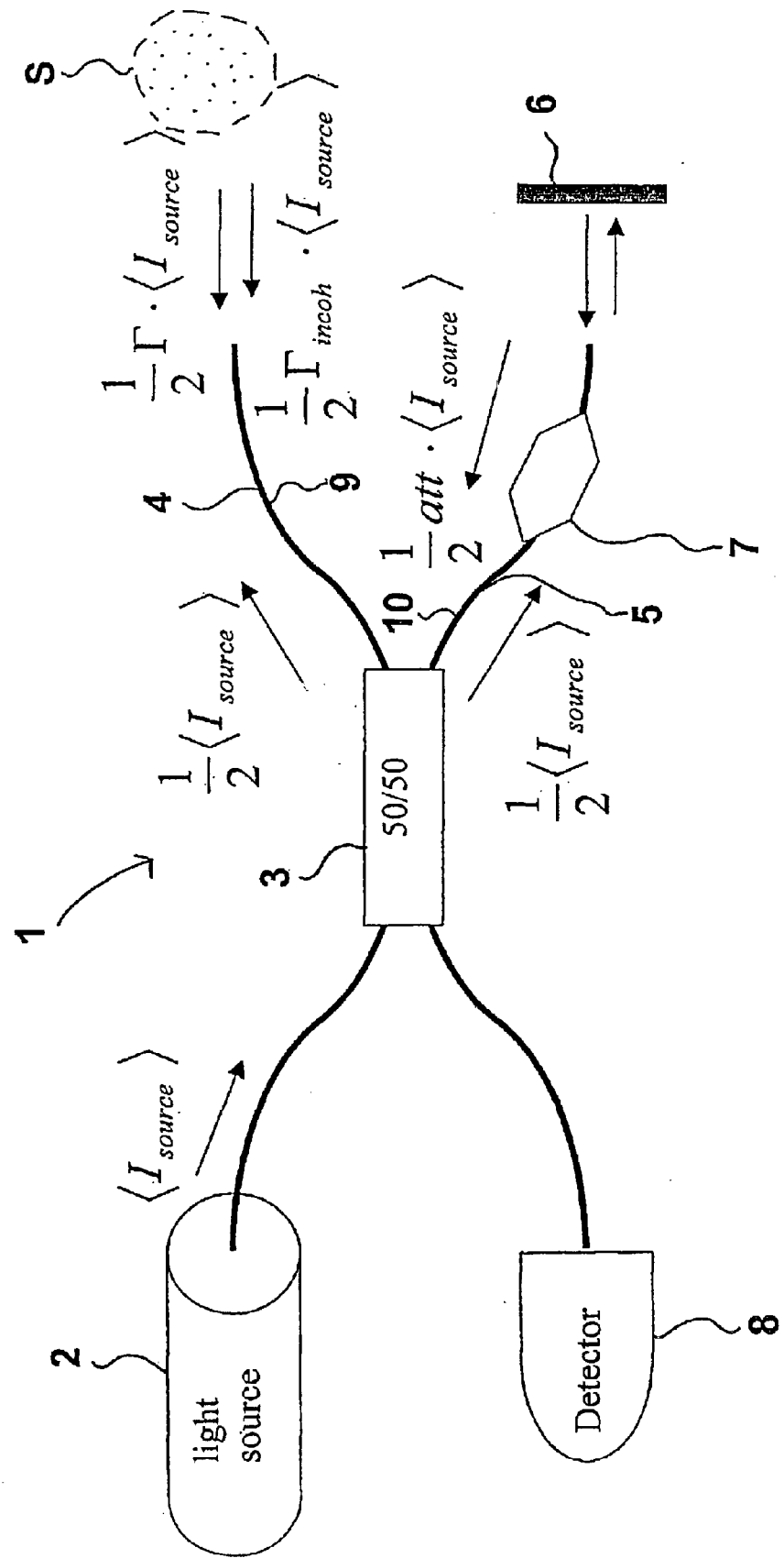
In FIG. 1 an unbalanced detection scheme, not according to the invention, is shown for comparison reasons. The optical coherence system is denoted 1. A light source 2 provides a light signal that is directed to a splitting means 3 for dividing said light signal into a first light field 4 and a second light field 5. The splitting ratio in FIG. 1 is set to 50/50. The first reflected light 9 and the second reflected light 10 is combined by the splitter means 3 and a combined signal is directed to the detector 8. The second reflected light field reflected from the reflection means 6 is attenuated by attenuator 7.
Figure 2:
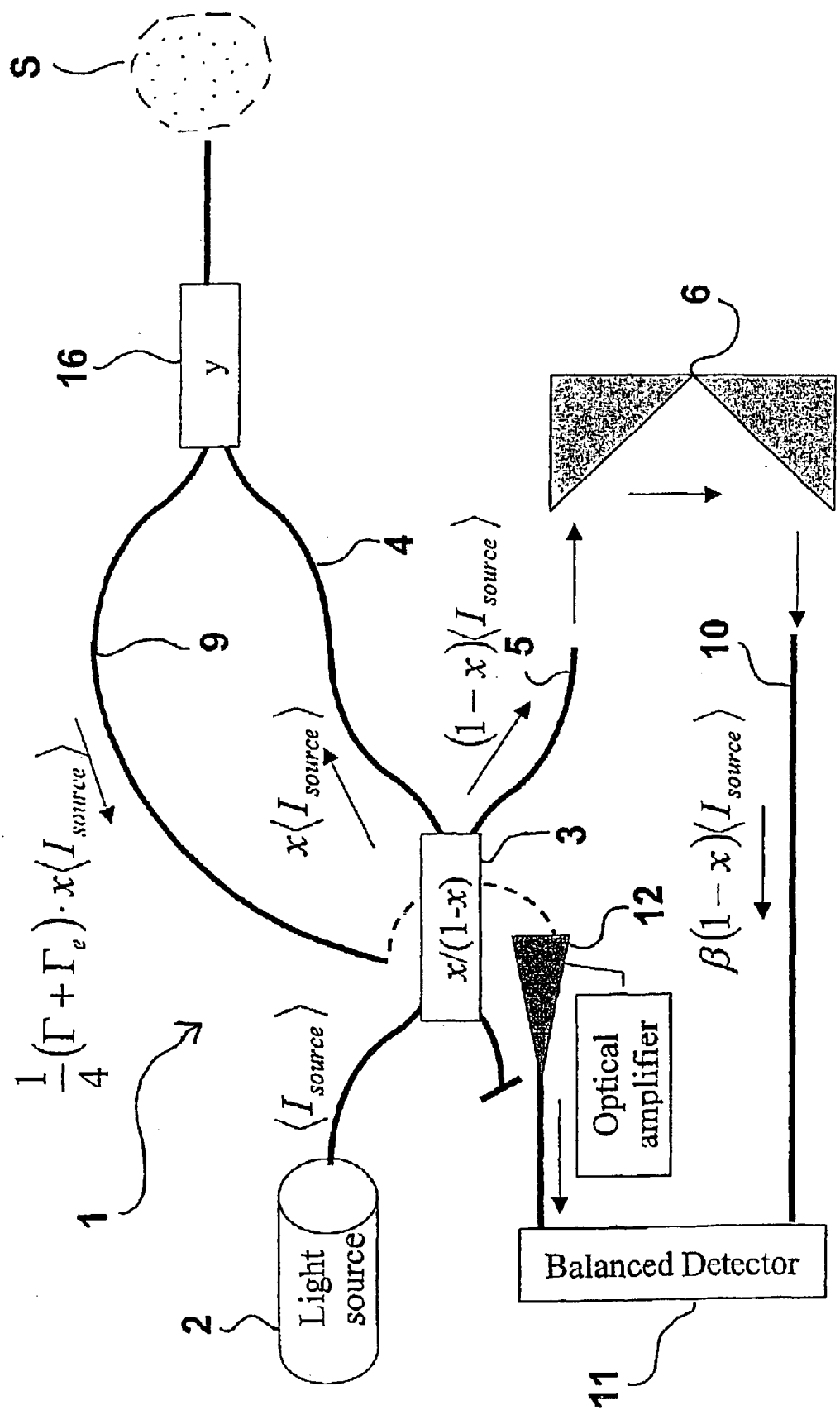
In FIG. 2 a detection scheme according to the invention is depicted. The optical coherence system is denoted 1. A light source 2 provides a light signal that is directed to a splitting means 3 for dividing said light signal into a first light field 4 and a second light field 5. The splitting ratio may be set to any suitable ratio, exemplified by the ratio x/1−x. The first reflected light field 9 is directed to a balanced detection means 11 comprising a combining means. An amplifier 12 is inserted in the first reflected light field to amplify the light signal reflected from the sample. A directing means 16 is inserted in the first light field 4 for directing the light field 4 to the sample and direct the reflected light field 9 to the optical amplifier 12. The second reflected light field 10 reflected from the reflection means 6 is also directed to the balanced detection means 11 comprising a combining means. The reflection means 6 is shown as a so-called corner cube configuration.

In the graphs in FIG. 6-FIG. 12, relative SNR implies that the system under investigation is compared to the corresponding reference system, which experiences the same conditions in terms of reflectivity, receiver noise etc. The novel system in FIG. 2 is compared to the reference system.

b) Optimum Splitting Ratio in the Absence of Amplification

Figure 6:
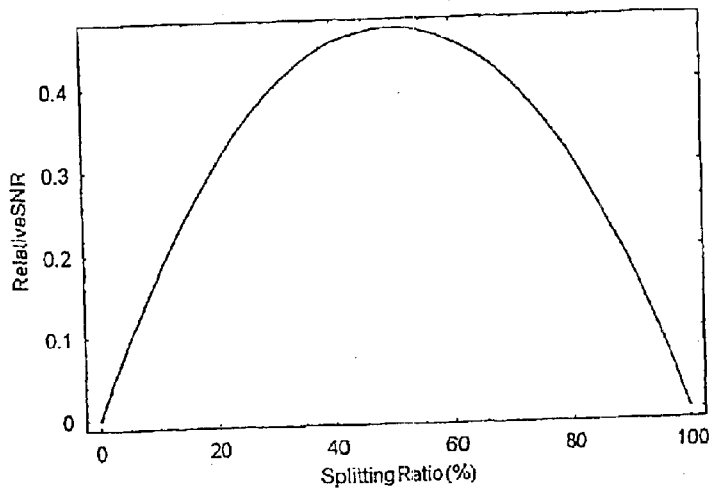
Figure 7:
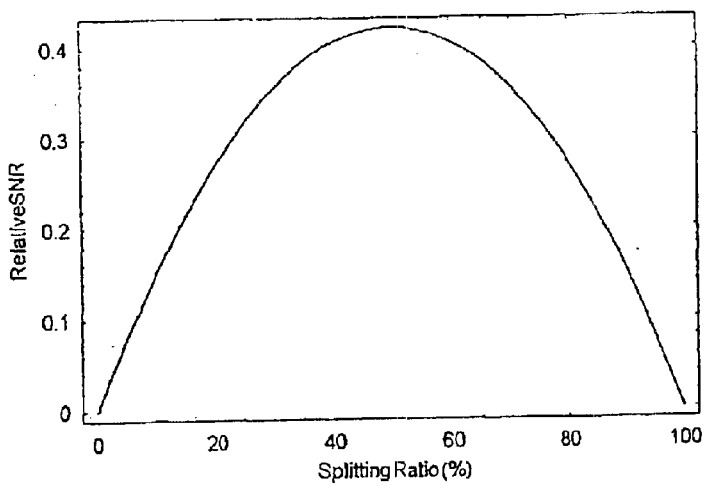

First, the splitting ratio x is investigated in the absence of an amplifier for both the coated and uncoated case. The SNR for this system is found from Eq (16) by letting $\chi=1$ and $I_{noise}=0$. FIGS. 6 and 7 shows the SNR of the system shown in FIG. 2 as a function of the splitter ratio x relative to the reference system FIG. 3 when $\Gamma_{noise}$ is in the uncoated and coated case, respectively.

From FIGS. 6 and 7 it is concluded that when an optical amplifier is not present in the system adjusting the splitting ratio away from 50/50 is a disadvantage.

c) Effect of Amplification for a Constant Splitting Ratio

Figure 8:
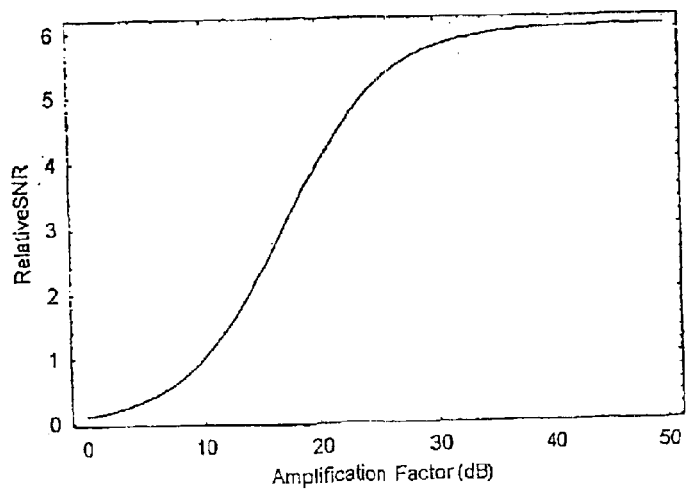
Figure 9:
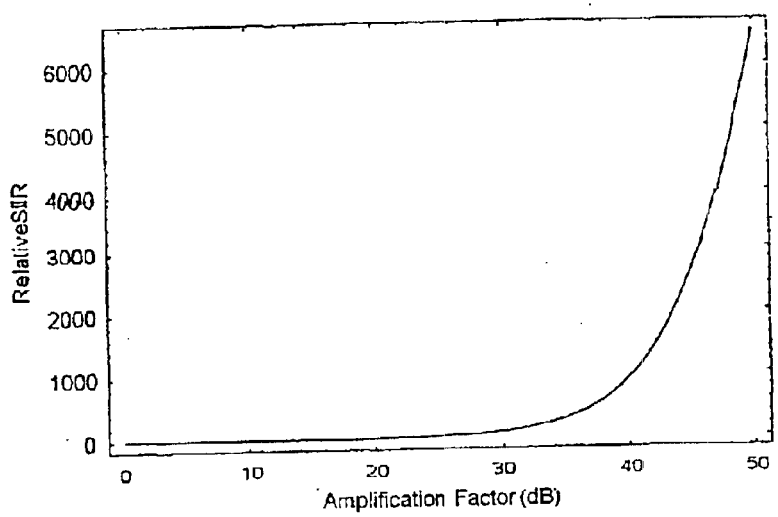

Next, the effect of the amplifier is investigated over a wide range of amplification factors and the splitting ratio is set to 50/50. FIG. 8 shows the increase in SNR due to the use of an optical amplifier in the system shown in FIG. 2 for the uncoated case and FIG. 9 shows the increase in SNR in the coated case. It is noted that the relative SNR is less than unity for low amplification factors. This is due to the amplifier having to compensate for the loss of optical signal power due to the extra coupler in the system under investigation and added amplifier noise.

d) Optimum Splitting Ratio for a Fixed Amplification

Figure 10:
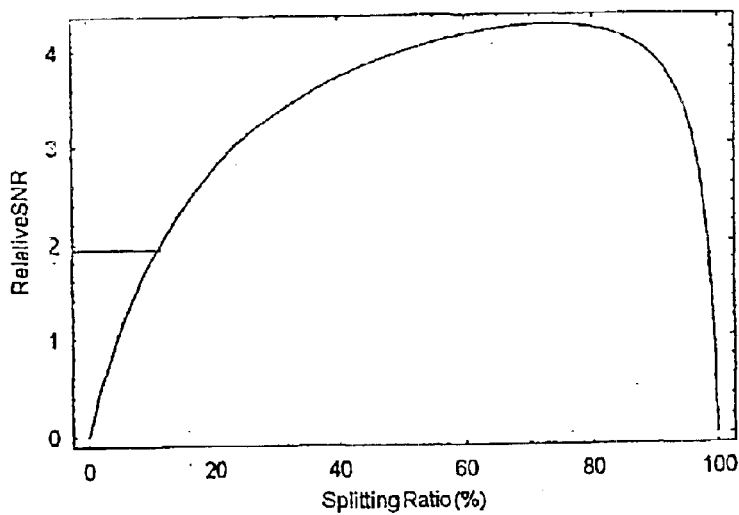
Figure 11:
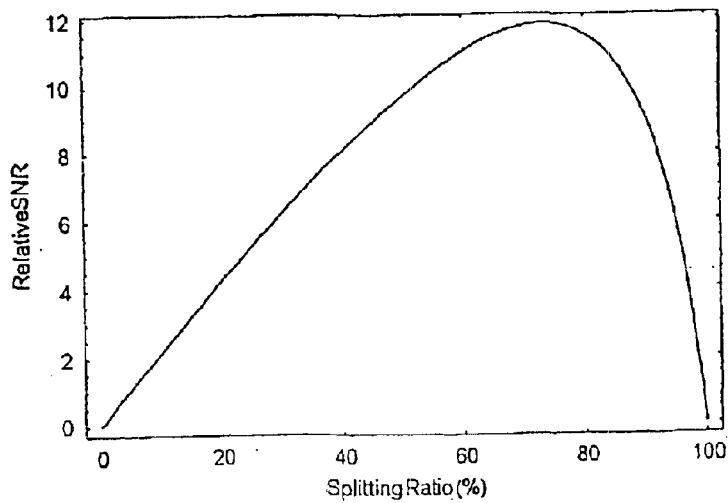

A conservative amplification factor of 100 (20 dB) is chosen and the effect of choosing a different splitting ratio than 50/50 is investigated again. FIG. 10 and FIG. 11 shows the uncoated and the coated case, respectively. These graphs demonstrate that in both cases it is an advantage to select a different splitting ratio then 50/50 for a system using optical amplification, and that the advantage of doing this is highest in the coated case. It is also seen that the increase in the relative SNR is about 400% higher for the coated case compared with the uncoated case.

e) Optical Circulators and Fixed Amplification

Another realization of the novel OCT system is shown in FIG. 4, where the y-coupler in the sample part has been replaced with a so-called optical circulator known from the art. Obviously, the signal light power is increased by a factor of four. Using the same parameters as above in d) for the coated case, the improvement in relative SNR for the realization in FIG. 4 is 44 compared to 12 for the realization in FIG. 2 when both realizations are compared to the same reference system.

Figure 12:
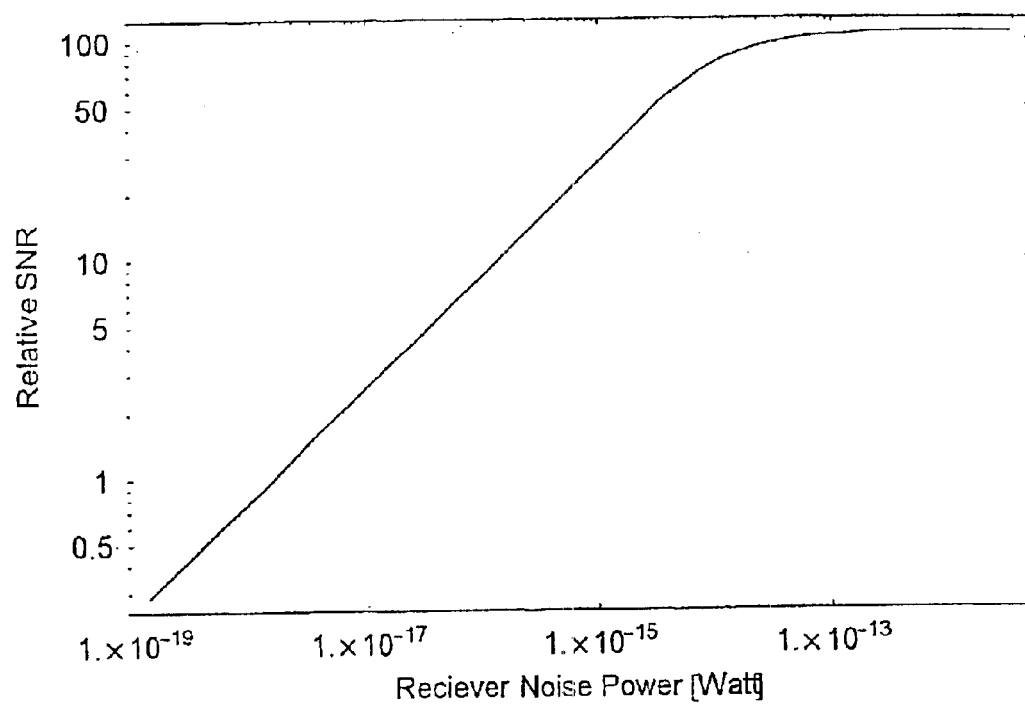

Finally, in FIG. 12 the sensitivity of the relative SNR on the receiver noise is demonstrated for the realization in FIG. 4. For a low thermal noise the optical amplifier may be a disadvantage since the noise is dominated by the noise added by the optical amplifier. As the thermal noise in the receiver is increased the optical amplifier becomes an increased advantage because the optical noise added is gradually masked by the thermal noise. For high values of the thermal noise the advantage of the optical amplifier is constant since the thermal noise is the dominant noise term.

Example 1b
a) Choice of Reference System

First, a reference system against which to compare the performance is decided. This system can be seen in FIG. 5. Through a similar analysis as to the one used to derive Eq. 16, where the amplification has been set to one and $I_{noise}$ is set to zero, the SNR of the system may be found. By doing so, it is found that the optimum splitting ratio toward the sample is approximately 35% and 65% toward the sample for the coated and for the uncoated case. This is shown in FIGS. (14) and (15) where $\Gamma_{incoh}$ is in the uncoated and coated case, respectively. A system with this splitting ratio is chosen as the reference system.

In the graphs in FIG. 16-FIG. 22, relative SNR implies that the system under investigation is compared to the corresponding reference system, which experiences the same conditions in terms of reflectivity, receiver noise etc. The novel system in FIG. 13 is compared to the reference system.

c) Effect of Amplification for a Constant Splitting Ratio

Next, the effect of the amplifier is investigated over a wide range of amplification factors and the splitting ratio is set to 50/50. FIG. 8 shows the increase in SNR due to the use of an optical amplifier in the system shown in FIG. 2 for the uncoated case and FIG. 9 shows the increase in SNR in the coated case. It is noted that the relative SNR is less than unity for low amplification factors. This is due to the amplifier having to compensate for the extra noise added by the amplifier, which for simplicity is assumed independent of amplification ratio.

d) Optimum Splitting Ratio for a Fixed Amplification

A conservative amplification factor of 100 (20 dB) is chosen and the effect of choosing a different splitting ratio than 50/50 is investigated again. FIG. 10 and FIG. 11 shows the uncoated and coated case, respectively. These graphs demonstrate that in both cases it is an advantage to select a different splitting ratio than 50/50 for a system using optical amplification although for chosen system parameters, the advantage is only slight and the optimum splitting ratio is 45/55. It is seen that the relative increase in SNR by inclusion of an optical amplifier is approximately a factor 5 higher in the coated case compared to the uncoated case.

e) Optical Circulators and Fixed Amplification

Another realization of the novel OCT system is shown in FIG. (4), where an optical circulator is inserted to avoid any reduction in the light power from the sample by the splitter. FIG. (12) and FIG. (13) shows the SNR of this system in the uncoated and coated case, respectively, where all other parameters are the same as where used for FIG. (18) and (19). In both cases, it is an advantage to select a splitting ratio significantly different from 50/50, and the advantage of doing so is greatest in the coated case. The advantage of inclusion of an optical amplifier is seen to be a factor 9 higher in the coated case compared to the uncoated case.

Figure 22:
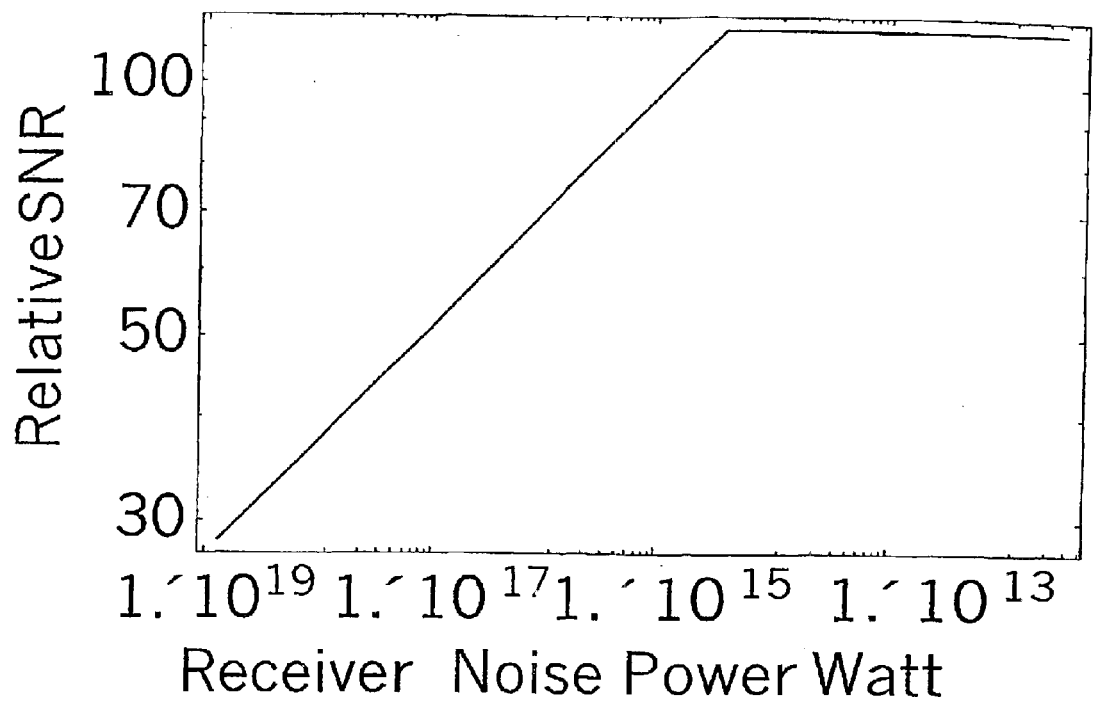

Finally, in FIG. 22 the sensitivity of the relative SNR on the receiver noise is demonstrated for the realization in FIG. 4. For a low thermal noise the optical amplifier may be a disadvantage since the noise is dominated by the noise added by the optical amplifier. As the thermal noise in the receiver is increased the optical amplifier becomes an increased advantage because the optical noise added is gradually masked by the thermal noise. For high values of the thermal noise the advantage of the optical amplifier is constant since the thermal noise is the dominant noise term.

The systems analyzed above should be considered typical examples. However, the advantage of introducing an optical amplifier is clearly pointed out. Firstly, it is demonstrated that the optical amplifier may aid to overcome receiver noise leading to improved system performance in terms increased SNR. The impact of optical amplification on an OCT system is highly dependent on the noise contribution from the receiving system, which comprises all components involved in obtaining an electrical signal from the optical output e.g. electrical amplifiers, computer data collection system etc. This sensitivity is illustrated through FIG. 22, where the system with optical amplifier and optical circulator (shown in FIG. 4) is compared to the reference system in the coated case. Secondly, an optimum splitting ratio different from 50/50 has been demonstrated. Finally, adding an optical amplifier will be an increased advantage as the electrical bandwidth of the receiver is increased, which may lead to an increase of the receiver noise. In other words, the optical amplifier may to a certain extent aid to overcome the increase in receiver noise. An increase in electrical detection bandwidth is necessary when fast acquisition of measurement data desired e.g. for real-time imaging.

What is claimed is:

1. An apparatus for optical coherence reflectometry comprising
   a light source for providing a light signal
   splitting means for dividing said light signal into a first light field and a second light field,
   means for directing the first light field to a sample, and means for directing a first reflected light field from the sample, wherein an optical amplifier is inserted in the first reflected light field, said optical amplifier being different from the light source, and means for directing the amplified first reflected light field to a combining means, so that the amplified first reflected light field is directed to the combining means through another route than a route through the splitting means for dividing the light signal,
   means for directing the second light field to a reference path comprising a reflecting means, and means for directing a second reflected light field from the reference path to the combining means,
   combining means for receiving said amplified first reflected light field and said second reflected light field to generate a combined light signal, and
   at least one detecting means for detecting the combined light signal and outputting detecting signals.

2. The apparatus according to claim 1, wherein the light source is a light emitting diode, a super luminescent diode, other white light sources of suitable wavelength or a short-pulse laser.

3. The apparatus according to claim 1, wherein the optical amplifier is a semiconductor resonator, amplifier, resonant amplifier, fibre and/or Raman amplifier.

4. The apparatus according to claim 1, wherein the first light field is directed to the sample without being amplified.

5. The apparatus according to claim 1, wherein substantially all light energy from the first reflected light field is directed to the combining means.

6. The apparatus according to claim 1, wherein substantially all light energy from the second reflected light field is directed to the combining means.

7. The apparatus according to claim 1, wherein the reflecting means of the reference path is a mirror or a retroreflector.

8. The apparatus according to claim 1, comprising means for altering the optical length of the reference path.

9. The apparatus according to claim 1, wherein the splitting means is bulk-optic, fibre optic or a hologram.

10. The apparatus according to claim 1, wherein the splitting ratio of the splitting means is substantially 50%/50%.

11. The apparatus according to claim 1, wherein the splitting ratio of the splitting means is changeable, so that from 1% to 99% of the light energy from the light source is directed to the sample arm.

12. The apparatus according to claim 11, wherein more than 50% of the light energy is directed to the sample.

13. The apparatus according to claim 1, wherein two detecting means are arranged to obtain a balanced detection signal.

14. The apparatus according to claim 1, wherein at least one CCD camera is arranged as a part of the detecting means to detect a part of the first reflected light field.

15. The apparatus according to claim 1, wherein at least a part of the means for directing the first light field is an optical fibre.

16. The apparatus according to claim 15, further comprising means for reducing non-sample reflection.

17. The apparatus according to claim 16, wherein the fibre-ends are anti-reflection coated.

18. The apparatus according to claim 16, wherein the fibre-ends are cleaved at an angle.

19. The apparatus according to claim 18, wherein the angle is at least 5 degrees.

20. The apparatus according to claim 1, further comprising an actuator means for moving the apparatus in a direction substantially parallel to the sample.

21. The apparatus according to claim 1, further comprising an actuator means for moving the apparatus in a direction substantially perpendicular to the sample.

22. The apparatus according to claim 1, further comprising processing means for providing a result of the detection signals.

23. The apparatus according to claim 22, further comprising a display device displaying the result from the processed detection signals.

24. A method for providing a result of a sample comprising
   establishing a light source for providing a light signal,
   splitting said light signal into a first light field and a second light field,
   directing the first light field to a sample, and the second light field to a reference path,
   receiving the first reflected light field from the sample,
   optically amplifying the first reflected light field,
   receiving the second reflected light field,
   combining said amplified first reflected light field and said second reflected light field to generate a combined light signal,
   detecting the combined light signal obtaining detection signals, and
   processing the detection signals obtaining the result image of the sample.

25. The method according to claim 24, wherein the sample is skin or mucosa.

26. The method according to claim 24, wherein the sample is retina.

27. The method according to claim 24, wherein the sample is a vessel or heart.

28. The method according to claim 24, applied during a surgical operation.

29. The method according to claim 24, wherein the sample is a polymer.

30. The method according to claim 24, wherein the sample is a silicon-based integrated circuit.

31. The method according to claim 24, wherein the sample is an integrated optical device.

32. The method according to claim 24, wherein the sample is an optical waveguide.

33. The method according to claim 24, wherein the light source is a light emitting diode, a super luminescent diode, other white light sources of suitable wavelength or a short-pulse laser.

34. The method according to claim 24, wherein the optical amplifier is a semiconductor resonator, amplifier, resonant amplifier, fibre and/or Raman amplifier.

35. The method according to claim 24, wherein the first light field is directed to the sample without being amplified.

36. The method according to claim 24, wherein substantially all light energy from the first reflected light field is directed to the combining means.

37. The method according to claim 24, wherein substantially all light energy from the second reflected light field is directed to the combining means.

38. The method according to claim 24, wherein the reflecting means of the reference path is a mirror or a retroreflector.

39. The method according to claim 24, comprising means for altering the optical length of the reference path.

40. The method according to claim 24, wherein the splitting means is bulk-optic, fibre optic or a hologram.

41. The method according to claim 24, wherein the splitting ratio of the splitting means is substantially 50%/50%.

42. The method according to claim 24, wherein the splitting ratio of the splitting means is changeable, so that from 1% to 99% of the light energy from the light source is directed to the sample arm.

43. The method according to claim 42, wherein more than 50% of the light energy is directed to the sample.

44. The method according to claim 24, wherein two detecting means are arranged to obtain a balanced detection signal.

45. The method according to claim 24, wherein at least a part of the means for directing the first light field is an optical fibre.

46. The method according to claim 45, further comprising means for reducing non-sample reflection(s).

47. The method according to claim 46, wherein the fibre-ends are anti-reflection coated.

48. The method according to claim 45, wherein the fibre-ends are cleaved at an angle.

49. The method according to claim 48, wherein the angle is at least 5 degrees.

50. The method according to claim 24, further comprising an actuator means for moving the first light field in a direction substantially parallel to the sample.

51. The method according to claim 24, further comprising an actuator means for moving the first light field in a direction substantially perpendicular to the sample.

52. The method according to claim 24, wherein the wavelength of the light source is in the range from 500 nm to 2000 nm.

53. The method according to claim 24, wherein the wavelength of the light source is in the range from 1250 nm to 2000 nm.

54. The method according to claim 24, wherein the wavelength of the light source is in the range from 600 nm to 1100 nm.

55. An apparatus for optical coherence reflectometry comprising:

a light source for providing a light signal, splitting means for dividing said light signal into a first light field and a second light field, means for directing the first light field to a sample, means for directing a first reflected light field from the sample, and means for reducing fibre-end reflection, wherein an optical amplifier is inserted in the first reflected light field, said optical amplifier being different from the light source, and means for directing the amplified first reflected light field to a combining means, so that the amplified first reflected light field is directed to the combining means through another route than a route through the splitting means for dividing the light signal, means for directing the second light field to a reference path comprising means for altering the optical path length, and means for directing a second light field from the reference path to the combining means, combining means for receiving said amplified first reflected light field and said second reflected light field to generate a combined light signal, and at least one detecting means for detecting the combined light signal and outputting detection signals.

* * * * *